US010191013B2

(12) United States Patent
Tansel et al.

(10) Patent No.: US 10,191,013 B2
(45) Date of Patent: Jan. 29, 2019

(54) IMPLEMENTATION OF HETERODYNE EFFECT IN SHM AND TALKING SHM SYSTEMS

(71) Applicants: Ibrahim Tansel, Coral Gables, FL (US); Volkan Senyurek, Miami, FL (US); Muhammed Unal, Miami, FL (US); Amin Baghalian, Miami, FL (US); Shervin Tashakori, Miami, FL (US)

(72) Inventors: Ibrahim Tansel, Coral Gables, FL (US); Volkan Senyurek, Miami, FL (US); Muhammed Unal, Miami, FL (US); Amin Baghalian, Miami, FL (US); Shervin Tashakori, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/592,438

(22) Filed: May 11, 2017

(65) Prior Publication Data
US 2018/0328892 A1 Nov. 15, 2018

(51) Int. Cl.
*G01N 29/12* (2006.01)
*G01N 29/44* (2006.01)

(52) U.S. Cl.
CPC ......... *G01N 29/12* (2013.01); *G01N 29/4445* (2013.01); *G01N 2291/0289* (2013.01)

(58) Field of Classification Search
CPC ........................... G01N 29/12; G01N 29/4445

USPC ....................................................... 73/579
See application file for complete search history.

(56) References Cited

U.S. PATENT DOCUMENTS

| | | | |
|---|---|---|---|
| 1,991,892 | A | 2/1935 | Fessenden |
| 3,469,229 | A | 9/1969 | Pure et al. |
| 3,836,951 | A | 9/1974 | Geren et al. |
| 5,885,129 | A | 3/1999 | Norris |
| 5,889,870 | A | 3/1999 | Norris |
| 5,973,999 | A | 10/1999 | Naff et al. |
| 2004/0247140 | A1 | 12/2004 | Norris et al. |
| 2011/0235465 | A1 | 9/2011 | Bostick et al. |
| 2014/0043183 | A1 | 2/2014 | Stolarczyk et al. |

OTHER PUBLICATIONS

Jiao et al., "ChinaContact defect detection in plates using guided wave and vibro-acoustic modulation," 17th World Conference on Nondestructive Testing, Oct. 25-28, 2008, pp. 1-7, Shanghai, China.
Zaitsev et al., "Novel nonlinear-modulation acoustic technique for crack detection," NDT&E International, Apr. 2006, pp. 184-194, vol. 39.
Donskoy et al., "Nonlinear acoustic interaction on contact interfaces and its use for nondestructive testing," NDT&E International, Jun. 2001, pp. 231-238, vol. 34.

(Continued)

*Primary Examiner* — John Chapman, Jr.
(74) *Attorney, Agent, or Firm* — Saliwanchik, Lloyd & Eisenschenk

(57) ABSTRACT

Systems and methods for implementation of the heterodyne effect in structural health monitoring (SHM) systems are provided. A system or method can include propagating a first signal with a first frequency and a second signal with a second frequency through a subject structure, and analyzing the output response to determine if a third frequency has been created, according to the heterodyne effect.

4 Claims, 10 Drawing Sheets

(56) References Cited

OTHER PUBLICATIONS

Verbiest et al., "Beating beats mixing in heterodyne detection schemes," Nature Communications, Mar. 10, 2015, pp. 1-5, vol. 6.

Hitchman et al., "Heterodyne interferometry for the detection of elastic waves: a tutorial and open-hardware project," European Journal of Physics, Mar. 9, 2015, pp. 1-13, vol. 36.

Okoshi, "Recent advances in coherent optical fiber communication systems," Journal of Lightwave Technology, Jan. 1987, pp. 44-52, vol. 5, No. 1.

Sakai, "Investigations of bolt loosening mechanisms (1st report, on the bolts of transversely loaded joints)," Bulletin of the JSME, Sep. 1978, pp. 1385-1390, vol. 21, No. 159.

Raghavan et al., "Review of guided-wave structural health monitoring," The Shock and Vibration Digest, Mar. 2007, pp. 91-114, vol. 39, No. 2.

Yan et al., "Structural health monitoring using high-frequency electromechanical impedance signatures," Advances in Civil Engineering, Feb. 2010, pp. 1-11.

Fekrmandi et al., "Inspection of the integrity of a multi-bolt robotic arm using a scanning laser vibrometer and implementing the surface response to excitation method (SuRE)," International Journal of Prognostics and Health Management, 2014, pp. 1-10.

Fekrmandi et al., "A non-contact method for part-based process performance monitoring in end milling operations," International Journal of Advanced Manufacturing Technology, Jul. 19, 2015, pp. 1-8.

Giurgiutiu et al., "Piezoelectric wafer embedded active sensors for aging aircraft structural health monitoring," Structural Health Monitoring, Jul. 2002, pp. 41-61, vol. 1, No. 1.

Giurgiutiu, "Structural health monitoring with piezoelectric wafer active sensors—predictive modeling and simulation," INCAS Bulletin, 2010, pp. 31-44, vol. 2, No. 3.

Ben et al., "Damage identification in composite materials using ultrasonic based lamb wave method," Measurement, Feb. 2013, pp. 904-912, vol. 46.

Staszewski et al., "Health monitoring of aerospace composite structures—active and passive approach," Composites Science and Technology, Article in Press, Sep. 2008, pp. 1-8.

Liu et al., "Guided waves based diagnostic imaging of circumferential cracks in small-diameter pipe," Ultrasonics, Article in Press, Oct. 2015, pp. 1-9.

Liu et al., "Circumferential and longitudinal defect detection using T(0,1) mode excited by thickness shear mode piezoelectric elements," Ultrasonics, Dec. 2006, pp. e1135-e1138, vol. 44.

Ma et al., "The reflection of guided waves from simple dents in pipes," Ultrasonics, Mar. 2015, pp. 190-197, vol. 57.

Ratassepp et al., "Scattering of the fundamental torsional mode at an axial crack in a pipe," The Journal of the Acoustical Society of America, Feb. 2010, pp. 730-740, vol. 127, No. 2.

Stoyko et al., "Detecting and describing a notch in a pipe using singularities," International Journal of Solids and Structures, Aug. 2014, pp. 2729-2743, vol. 51.

Fekrmandi et al., "Investigation of the computational efficiency and validity of the surface response to excitation method," Measurement, Feb. 2015, pp. 33-40, vol. 62.

Chakraborty et al., "Damage classification structural health monitoring in bolted structures using time-frequency techniques," Journal of Intelligent Material Systems and Structures, Jul. 2009, pp. 1289-1305, vol. 20.

Kessler et al., "Damage detection in composite materials using lamb wave methods," Smart Materials and Structures, Apr. 2002, pp. 1-24.

Giurgiutiu, "Structural health monitoring with piezoelectric wafer active sensors," Proceedings of the 16th International Conference of Adaptive Structures and Technologies, Oct. 10-12, 2005, pp. 1-8, Paris, France.

Li et al., "Propagation of guided waves in pressure vessel," Wave Motion, Article in Press, Oct. 2014, pp. 1-13.

Giurgiutiu et al., "Electro-mechanical impedance method for crack detection in metallic plates," SPIE's 8th Annual International Symposium on Smart Structures and Materials and 6th Annual International Symposium on NDE for Health Monitoring and Diagnostics, Mar. 4-8, 2001, pp. 1-12, Newport Beach, California.

Tashakori et al., "Contact and non-contact approaches in load monitoring applications using surface response to excitation method," Measurement, Jul. 2016, pp. 197-203, vol. 89.

Xu et al., "Single mode tuning effects on lamb wave time reversal with piezoelectric wafer active sensors for structural health monitoring," Journal of Nondestructive Evaluation, Oct. 2007, pp. 123-134, vol. 26.

Guo et al., "Detection of fatigue-induced micro-cracks in a pipe by using time-reversed nonlinear guided waves: a three-dimensional model study," Ultrasonics, Sep. 2012, pp. 912-919, vol. 52.

Meo et al., "Nonlinear elastic wave spectroscopy identification of impact damage on a sandwich plate," Composite Structures, Dec. 2005, pp. 469-474, vol. 71.

Van Den Abeele et al., "Nonlinear elastic wave spectroscopy (NEWS) techniques to discern material damage. Part II: single mode nonlinear resonance acoustic spectroscopy," Research in Nondestructive Evaluation, Sep. 2000, pp. 1-24, vol. 12, No. 1.

Liu et al., "Localization of material defects using nonlinear resonant ultrasound spectroscopy under asymmetric boundary conditions," Physics Procedia, Jan. 2010, pp. 55-61, vol. 3.

Houhat et al., "One-dimensional parametric study of damage detection in a solid material using a nonlinear wave modulation spectroscopy (NWMS) technique," 4th International Conference on Electrical Engineering, Dec. 13-15, 2015, pp. 1-4.

Liu et al., "Noncontact detection of fatigue cracks by laser nonlinear wave modulation spectroscopy (LNWMS)," NDT&E International, Sep. 2014, pp. 106-116, vol. 66.

Straka et al., "Detection of structural damage of aluminum alloy 6082 using elastic wave modulation spectroscopy," NDT&E International, Sep. 2008, pp. 554-563, vol. 41.

Gabor, "Theory of communication. Part 1: the analysis of information," Journal of the Institution of Electrical Engineers—Part III: Radio and Communication Engineering, Nov. 1946, pp. 429-441, vol. 93, No. 26.

Fekrmandi et al., "A novel approach for classification of loads on plate structures using artificial neural networks," Measurement, Mar. 2016, pp. 37-45, vol. 82.

Siqueira et al., "The use of ultrasonic guided waves and wavelets analysis in pipe inspection," Ultrasonics, May 2004, pp. 785-797, vol. 41.

Ahmad et al., "Structural health monitoring of steel pipes under different boundary conditions and choice of signal processing techniques," Advances in Civil Engineering, Dec. 2012, pp. 1-14.

Kim et al., "Health monitoring of axially-cracked pipes by using helically propagating shear-horizontal waves," NDT&E International, Mar. 2012, pp. 115-121, vol. 46.

Lee et al., "Application of laser-generated guided wave for evaluation of corrosion in carbon steel pipe," NDT&E International, Apr. 2009, pp. 222-227, vol. 42.

Baltazar et al., "Structural health monitoring in cylindrical structures using helical guided wave propagation," Physics Procedia, May 2015, pp. 686-689, vol. 70.

Jin et al., "Time reversal data communications on pipes using guided elastic waves—Part 1: basic principles," Proceedings of SPIE, Mar. 2011, pp. 1-12, vol. 7984.

Biwa et al., "On the acoustic nonlinearity of solid-solid contact with pressure-dependent interface stiffness," Transactions of the ASME, Journal of Applied Mechanics, Jul. 2004, pp. 508-515, vol. 71.

Kim et al., "Experimental characterization of fatigue damage in a nickel-base superalloy using nonlinear ultrasonic waves," The Journal of the Acoustical Society of America, Sep. 2006, pp. 1266-1273, vol. 120, No. 3.

Scholey et al., "Quantitative experimental measurements of matrix cracking and delamination using acoustic emission," Composites: Part A, May 2010, pp. 612-623, vol. 41.

Meo et al., "Detecting damage in Composite material using nonlinear elastic wave spectroscopy methods," Applied Composite Materials, Sep. 2008, pp. 115-126, vol. 15.

(56) References Cited

OTHER PUBLICATIONS

Zumpano et al., "Damage localization using transient non-linear elastic wave spectroscopy on composite structures," International Journal of Non-Linear Mechanics, Apr. 2008, pp. 217-230, vol. 43.

Su et al., "Guided lamb waves for identification of damage in composite structures: A review," Journal of Sound and Vibration, Aug. 2006, pp. 753-780, vol. 295.

Yang et al., "A synthetic time-reversal imaging method for structural health monitoring," Smart Materials and Structures, Mar. 2004, pp. 415-423, vol. 13.

Amerini et al., "Structural health monitoring of bolted joints using linear and nonlinear acoustic/ultrasound methods," Structural Health Monitoring, Jan. 2011, pp. 659-672, vol. 10, No. 6.

Polimeno et al., "Detecting barely visible impact damage detection on aircraft composites structures," Composite Structures, Dec. 2009, pp. 398-402, vol. 91.

Sohn et al., "Nonlinear ultrasonic wave modulation for online fatigue crack detection," Journal of Sound and Vibration, Feb. 2014, pp. 1473-1484, vol. 333.

Hajek et al., "Principles of a defect localisation in nonlinear ultrasonic mixing impulse spectroscopy," Advances in Military Technology, Dec. 2014, pp. 41-48, vol. 9, No. 2.

IMPLEMENTATION OF HETERODYNE EFFECT IN SHM AND TALKING SHM SYSTEMS

BACKGROUND

Structural Health Monitoring (SHM) systems were developed to monitor the condition of structures. They have been used to warn pilots about developing problems and to reduce maintenance costs by identifying problems in a timely manner. Traditional passive SHM systems require sensors, processors, and data analysis. Active systems use their own actuator to excite the system. Many SHM systems require baseline data and engineer operators to interpret the sensory signals successfully.

BRIEF SUMMARY

Embodiments of the subject invention provide devices, protocols, and methods for detection of defects in existing structures. Methods can detect the presence and location of structural defects, which gives the structure nonlinear characteristics. These defects include but are not limited to cracking, delamination, debonding, and loose bolts. The protocols and methods of embodiments of the subject invention use the heterodyne effect to reduce and eliminate the costs and complexity associated with traditional Structural Health Monitoring (SHM) techniques.

In an embodiment, a method of detecting structural defects can comprise exciting the surface of a plate at at least two different frequencies with sinusoidal signals. A function generator and/or at least one special purpose circuit can be used to generate the signal. The first and second frequencies can be configured to oscillate beyond the audible range of a person (i.e., audible range detectable by a person with an unaided ear (20 kHz)). If a structural defect, which gives the structure nonlinear characteristics, exists, the defect will act as a nonlinear mixer and create new frequencies, in accordance with the heterodyne effect. A third frequency, which is the second frequency minus the first frequency, will be created, according to the heterodyne effect. The first frequency and the second frequency can be configured such that the third frequency is within the audible range of a person. If the dynamic characteristics of the system allow the vibrations to be at a reasonable amplitude, the structure will create audible sound. There may be some oscillations at the harmonics of the mentioned three frequencies as well, but systems of the embodiments of the subject invention can function without the need to make use of such oscillations. The sound can be maximized by selecting the difference of the excitation frequencies at the natural frequency of the structure if it is in the 0-20 kHz range. Thus, the sound alerts a user to a structural defect in the subject structure. By leveraging the heterodyne effect, SHM systems can eliminate the need for sensors and costly data acquisition systems, provide sensorless detection, and generate audible signals that alert users to the defects creating nonlinear characteristics at the structure including cracks, delamination, loose bolts, and debonding. Composite materials or rigid plates may not vibrate at high amplitudes and may not create sound in certain cases (e.g., if no nonlinearity is present). In such a case, a sensor and/or simple hardware or software can be used to detect the presence and amplitude of the third frequency. Even if such a sensor or hardware is used, signal processing is still simpler than that in the related art, and there is no need for baseline or reference data collected at ideal conditions.

In another embodiment, a method of detecting structural defects can comprise embedding a verbal message through modulation into the first signal. The first signal and a second signal, can be propagated across a subject structure. If the first signal and the second signal pass over a structural defect, the defect will act as a nonlinear mixer, demodulate the modulated first signal and emit the verbal message, according to the heterodyne effect.

In another embodiment, the first and second signals at different frequencies are not be sent continuously. Only a small number (e.g., 3 or 4) of wavelengths are sent from the actuators at high frequencies. The waves can propagate over the surface, and they can intersect each other only at certain locations depending on the location of the actuators and the delay between the respective release times of the signals. This approach allows the inspection of the structure within small regions, and it depends on the wavelength and the number of waves. A sensor may be useful to collect and evaluate the data if the third frequency at the difference of the excitation signals exists. The arrival time of the signal to the sensor also helps estimation of the location of the defect.

DETAILED DISCLOSURE

Embodiments of the subject invention provide novel and advantageous protocols and methods for determining the presence and location of defects in critical structures. Structural defects include but are not limited to cracks, debonded structures, delaminated structures, or loose bolts. Defects in a system will cause a linear system to behave in a nonlinear fashion. The structure can be excited with at least two signals at different frequencies. If the target area does not contain structural defects that create nonlinear characteristics, (including but not limited to cracks, unintended openings, or loose fittings), the structure will exhibit linear behavior and the system will have only the frequencies of the excitation signals. No audible or visual output signal is produced. However, if a structural defect exists, as the two signals meet across the structural defect, the system will exhibit nonlinear behavior and create signals with new frequencies, according to the heterodyne effect. These new frequencies can be configured to create sound to alert a user.

Figure 1:
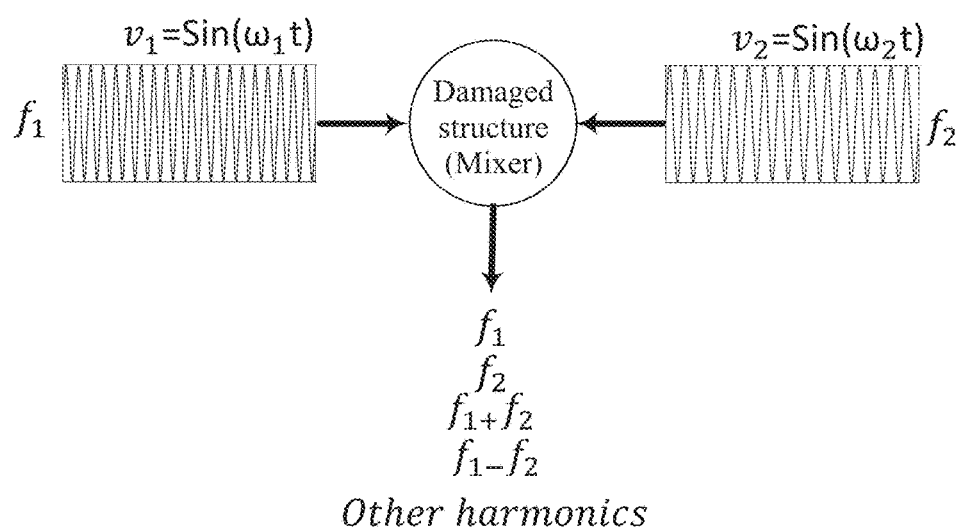
FIG. 1 shows a schematic drawing of a frequency mixer.

Heterodyning, or frequency conversion, is a signal processing technique developed by Reginald Fessenden in 1901. The heterodyning technique involves combining two signals with distinct frequencies in a non-linear signal processing device or mixer to create an output signal that contains new frequencies. FIG. 1 presents a diagram of a common application of a mixer. Input signal 1 at a first frequency ($f_1$) and input signal 2 at a second frequency ($f_2$) are applied to a mixer, and an output signal is produced. According to the heterodyne effect, if the mixer generates a non-linear response, then the output signal contains the first frequency ($f_1$), the second frequency ($f_2$), and additional frequencies. When the structure contains no defects, the structure behaves as a linear system. Waves may continuously propagate through the structure and, although the signals may lose amplitude, the output signal contains no new frequencies.

Some structural defects, however, disturb the linear characteristics of the system and cause the structure to behave as a nonlinear system. Signals propagating across these types of structural defects will disconnect momentarily due to the lack of continuous contact. When at least two signals propagate across this non-linearity, an output signal containing new frequencies is generated, according to the heterodyne effect.

Structural health monitoring (SHM) systems are employed to test and monitor the structural integrity of an existing structure and are traditionally characterized as active or passive SHM systems. Active SHM systems utilize actuators to introduce controlled and systematic excitation signals into a system. Sensors are strategically positioned to monitor the response at different points. Passive SHM systems use embedded sensors to monitor the ambient signals of the structure and detect deviations. Typical SHM systems components include sensor(s), processor(s), and a user interface. In both active and passive SHM systems, a data acquisition system digitizes the sensory signals and stores the data. After preprocessing data through filtering, amplifying, and normalization, signal characteristics are determined through mathematical and statistical methods. Most active and passive SHM methods require collection of base line data for comparison and interpretation with regularly collected signals. Base line or reference data is collected when the structure is in an ideal condition. Well-trained engineers or technicians interpret incoming signals to determine if a structural defect exists. Costs, complexity, bulkiness, and personnel constraints create feasibility issues that limit typical SHM systems to bridges, high rise buildings, aerospace designs, and special applications. Due to the known input, the active SHM system technique generally provides more reliable data than a passive SHM system.

Active SHM systems can be further subdivided into linear and non-linear methods. Early SHM methods, such as pitch-catch, pulse-echo, and electromechanical impedance methods, viewed structures as linear systems and assumed surface waves propagate along plates and bounce at interferences. Linear SHM methods rely on characters such as magnitude, phase, energy, and time of flight of propagating waves. Data for these parameters are retrieved and examined to determine the presence and location of defects. However, if the defect size is small or the test parameters are not chosen correctly, the linear methods are unable to accurately detect the defects. Furthermore, these methods are not effective for detecting signals changes in the early stages of development.

Nonlinear methods assume pristine plates behave as linear systems and the development of cracks, initial debonding, and loosening bolts cause the structure to behave as a nonlinear system. Nonlinear and non-destructive evaluation (NDE) methods analyze the characteristics of the harmonics, summations, and subtractions of the excitation frequencies to evaluate a structure for defects. The nonlinear NDE and SHM systems excite the structure with a combination of a high excitation frequency and a low (e.g., below 1 kHz) excitation frequency across a structure. Sensors monitor and retrieve data from the output response, and this data is analyzed to determine the presence and location of structural defects. Nonlinear NDE methods can detect development of structural defects such as fatigue cracks and early debonding at earlier stages than linear SHM methods.

When a structure contains no structural defects, the expected system response can be described as follows:

$$v_o = av_1 \pm bv_2 = a\sin(\omega_1 t) \pm b\sin(\omega_2 t),$$

where $v_o$ is the output response, $\omega_1$ and $\omega_2$ are the angular frequencies of the excitation frequencies, and t is time.

However, if structural defects exist, the defects act as a nonlinear mixer and the resulting response can be described as follows:

$$v_o = av_1 \pm bv_2 \pm (av_1 \pm bv_2)^2 \pm (av_1 \pm bv_2)^3 + \ldots = a\sin(\omega_1 t) \pm b\sin(\omega_2 t) \pm c(\cos(2\omega_1 t)) \pm d(\cos(2\omega_2 t)) \pm e(\cos((\omega_1+\omega_2)t)) \pm f(\cos((\omega_1-\omega_2)t)) + g + \ldots,$$

where $v_o$ is the output response, $\omega_1$ and $\omega_2$ are the angular frequencies of the excitation frequencies, and t is time.

Sensorless SHM (SSHM) systems of embodiments of the subject invention leverage the heterodyne effect to generate an audible response to alert a user that a structural defect exists. A user can select a first frequency and a second frequency that generate an output response with an audible third frequency if a structural defect exists. The SSHM protocols and methods of embodiments of the subject invention present cost effective, reliable, and convenient techniques for detecting early and late stage structural defects, while reducing the complexity of traditional SHM systems by eliminating sensors, preprocessing, data interpretation, and warning systems. Additionally, the simple audible response of the SSHM systems of embodiments of the subject invention allow for non-engineers to operate the system.

Figure 2:
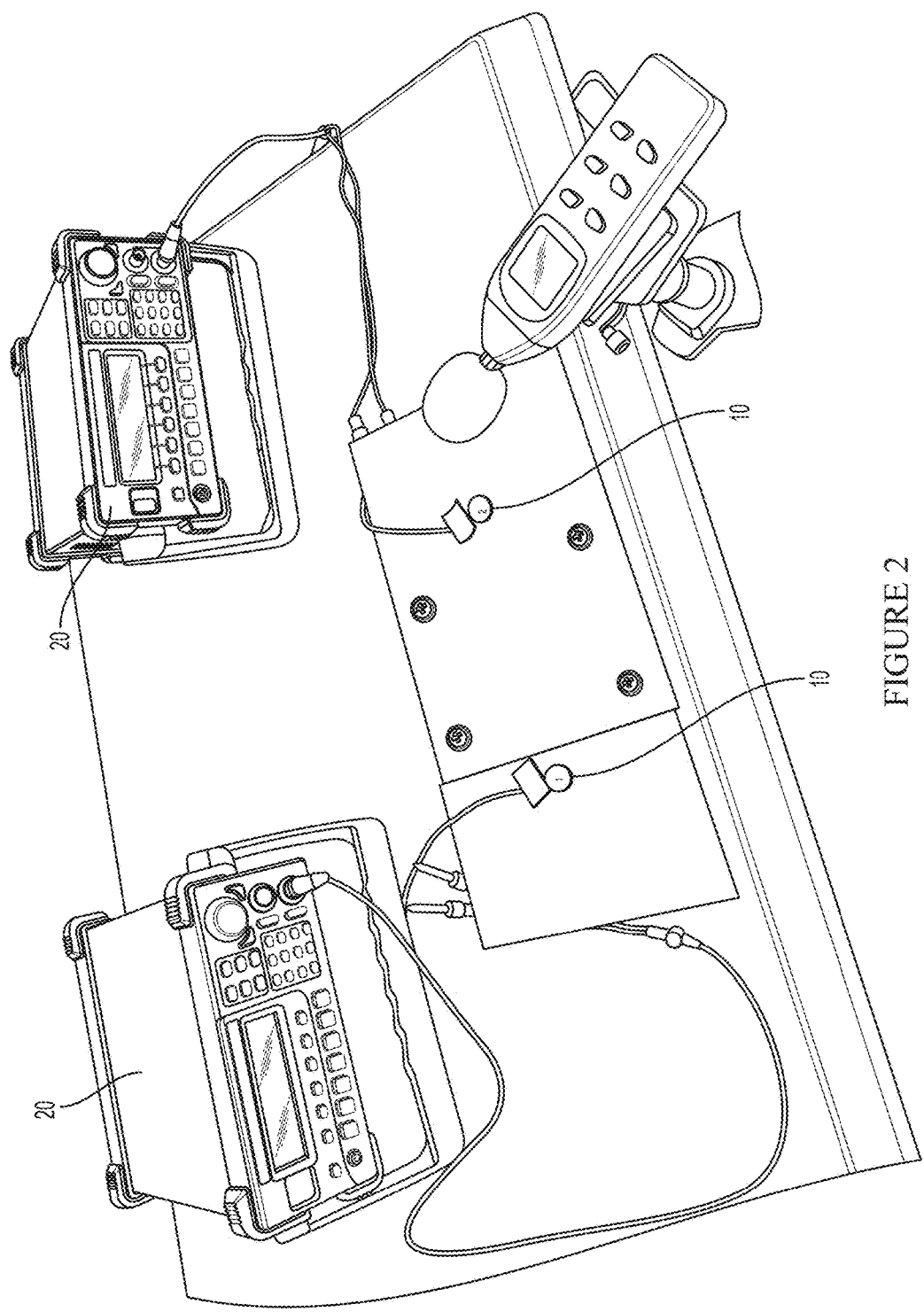
FIG. 2 shows an image of a sensorless structural health monitoring (SSHM) system according to an embodiment of the subject invention.

FIG. 2 shows an image of an SSHM system according to an embodiment of the subject invention. Two actuators 10 can be attached to the same plate. Each actuator 10 can be attached to a separate plate, and the two plates can be joined together by fasteners, such as bolts (e.g., four fasteners, such as four bolts). A structure can be a single object or separate objects joined by bolts or fasteners or another form of mechanical joint. The actuators 10 can comprise piezoelectric elements (PZTs), though embodiments are not limited thereto. The actuators 10 can be connected to at least one signal generator 20. A signal generator includes but is not limited to signal generators, function generators, and/or waveform generators. The signal generator can excite the actuators 10 with a first signal at a first frequency ($f_1$) and with a second signal at a second frequency ($f_2$). The first and second frequencies can be set above, for example 20 kilohertz (kHz) so as to be above the normal audible range of a person (i.e., the normal audible range detectable by a person with an unaided ear). When no structural defects exist, the output response will contain the first and second frequencies, which are outside the audible range of a person. If the subject structure contains a crack or if two components are not joined tightly, the system will behave as a non-linear system and the defect will act as a nonlinear mixer. As the first signal and the second signal meet at the structural defect, new frequencies are created. The output response will contain the first frequency, second frequency and at least a third frequency ($f_3$). The third frequency ($f_3$) can be equal to the second frequency ($f_2$) minus the first frequency ($f_1$). The first frequency ($f_1$) and the second frequency ($f_2$) can be configured so that the third frequency ($f_3$) is within the audible range and the resulting sound will be noticeable to a user.

In another embodiment of the subject invention, the SSHM system can detect the presence and location of structural defects. The signal generator 10,20 can transmit two harmonic signals for a very short time. For example, only three or four periods of the harmonic signal may be applied to create surface waves. The frequencies of the surface waves generated by the signal generator 10,20 can be different. Both waves can start from the piezoelectric element that creates them and can propagate along the surface. They can intersect each other at a certain region of the plate. The region where they overlap each other can be selected by adjusting the delay time between the release of the waves from each piezoelectric element. Only the region the waves overlap may be inspected. The size of the inspected region can be controlled by selecting the frequency of the excitation signals and the number of the released waves. If there are any defect(s) that give(s) non-linear characteristics to the structure at the inspected region, waves with new frequencies will be generated. Because the speed of the surface waves at a specific frequency and the delay time between the release of the surface waves are known, the inspected region can be calculated. A sensor can be put at any location on the plate. In addition, the time it takes the new waves to reach the sensor can help the estimation of the location where the waves are generated. The location of the defect can be estimated from the known location of the inspected region and arrival time of the waves with the new frequency to the sensor. The surface can be scanned electronically by selecting different delay times between the release of the waves from the exciters.

In an embodiment of the subject invention, the SSHM system can detect structural defects and deliver a warning sound (e.g., a single tone warning sound). A signal generator can be connected to at least two actuators connected to a subject structure. Each actuator can be excited with a first single tone signal at a first frequency ($f_1$) and second signal tone signal at a second frequency ($f_2$), respectively. The first frequency ($f_1$) and second frequency ($f_2$) can be above, for example, 20 kHz so as to be above the normal audible range of a user. If the structure contains a defect, the defect can act as a nonlinear mixer. As the first signal and the second signal meet at the structural defect, new frequencies are created. The output response will contain the first frequency, the second frequency, and at least a third frequency ($f_3$), according to the heterodyne effect. The third frequency ($f_3$) can be equal to the second frequency ($f_2$) minus the first frequency ($f_1$). The first frequency ($f_1$) and the second frequency ($f_2$) can be configured so that the third frequency ($f_3$) is within the audible range and produces a single tone sound to alert the user to the structural defect.

In another embodiment of the subject invention, the SSHM system can detect structural defects and deliver a warning signal (e.g., a pulsed tone warning signal). A signal generator can be connected to an actuator, which is connected to a subject structure, and which can excite the structure with an Amplitude Shift Key (ASK) modulated signal at the first signal ($f_1$) carrier frequency. A second actuator can excite the subject structure with a single tone signal at the second frequency ($f_2$). If the subject structure contains a structural defect, the system will behave as a non-linear system and the system will produce an output response that contains a third frequency ($f_3$), according to the heterodyne effect. This third frequency ($f_3$) can be the equal to the result of subtracting the second frequency ($f_2$) from the first frequency ($f_1$). The output response can produce a pulsed tone sound and alert the user to the structural defect.

In another embodiment of the subject invention, the SSHM system can detect structural defects and deliver a high-low siren type warning signal. A signal generator can be connected to an actuator that can excite a subject with a first signal, which can be a Frequency Shift Key (FSK) modulated signal at the first frequency ($f_1$). A second actuator can excite the subject structure with a single tone signal at a second frequency ($f_2$). If the subject structure contains a structural defect, the system can produce an output response with a third frequency ($f_3$), according to the heterodyne effect. The output response can produce an audible pattern of alternating high and low tones at a desired cycling rate. This sound is analogous to a high-low siren type sound.

In another embodiment of the subject invention, the SSHM system can detect structural defects and deliver a yelp siren warning signal. A signal generator can be connected to an actuator, which is connected to a subject structure, and which can excite the structure with frequency modulated sine signal at a first frequency ($f_1$). A second actuator can excite the subject structure with a single tone signal at a second frequency ($f_2$). If the subject structure contains a structural defect, the system will behave as a non-linear system and the system will produce an output response that contains a third frequency ($f_3$), according to the heterodyne effect. This third frequency ($f_3$) can be equal to the result of subtracting the second frequency ($f_2$) from the first frequency ($f_1$). The output response can produce a yelp warning sound and alert the user to the structural defect.

In further embodiments, a warning sound can be replaced with an embedded verbal message, music sounds, and/or other audible warnings. A signal generator can be connected to an actuator, which is connected to a subject structure, and which can excite the structure using a Single Side Band (SSB) technique to modulate a special verbal message at a first frequency ($f_1$). A second actuator can excite the structure with a signal at a second frequency ($f_2$), which may be a single tone signal also at the first frequency ($f_1$). If the subject structure contains a structural defect, the system can behave as a non-linear system and the system can produce an output response that contains a third frequency ($f_3$), according to the heterodyne effect. This third frequency can contain a special verbal message or other audible warning directed to the user.

Figure 3:
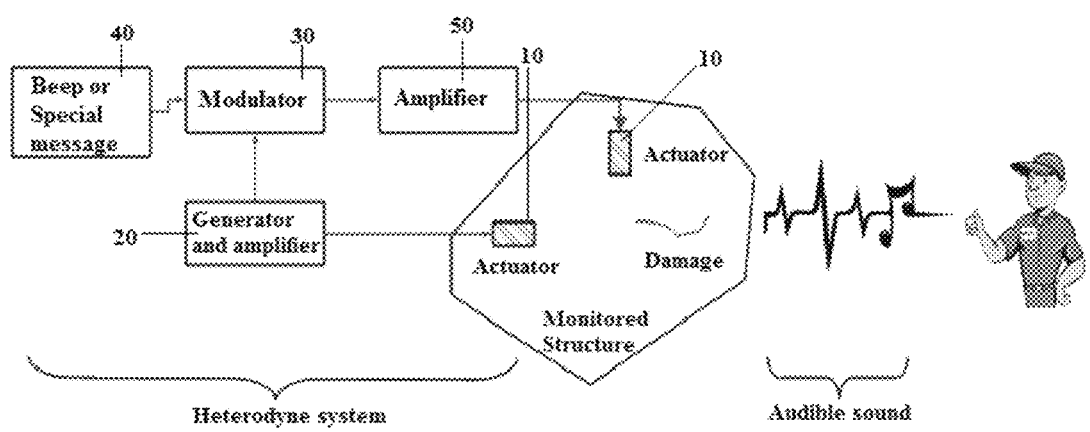
FIG. 3 shows a schematic view of an SSHM system according to an embodiment of the subject invention.

FIG. 3 shows a schematic view of an SSHM system according to another embodiment of the subject invention. Referring to FIG. 3, a signal generator 20 can emit a first signal at a first frequency ($f_1$), and a beep or special message 40 can be encoded into the first signal through modulation (e.g., by modulator 30) and passed through an amplifier 50 and emitted into a subject structure through an actuator 10. The signal generator 20 can emit a second signal at a second frequency ($f_2$) through a second actuator 10 to excite the subject structure. Damage to the monitored structure can act as a mixer and demodulate the message or create an alarm tone and transmit an audible sound to an end user.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes but is not limited to, the following exemplified embodiments.

Embodiment 1

A method for a structural health monitoring, the method comprising:
attaching a first signal generator to a first actuator connected to a subject structure;
generating a first signal at a first frequency with the first signal generator and a second signal at a second frequency with a second signal generator;
exciting the subject structure with the first signal (e.g., using the first actuator) and the second signal (e.g., using a second actuator connected or attached to the second signal generator); and
monitoring the output response for a third frequency.

Embodiment 2

The method according to embodiment 1, wherein the third frequency is equal to (or approximately equal to) the absolute value of the second frequency minus the first frequency.

Embodiment 3

The method according to any of embodiments 1-2, wherein the first frequency and the second frequency are higher than the highest frequency in the audible range of a person (i.e., the higher than the highest frequency a person can hear with an unaided ear).

Embodiment 4

The method according to any of embodiments 1-3, wherein the third frequency is within the audible range of a person.

Embodiment 5

The method according to any of embodiments 1-4, wherein, in order to produce a single tone sound, the first signal is a single tone signal and the second signal is a single tone signal.

Embodiment 6

The method according to any of embodiments 1-4, wherein, in order to produce a pulse tone sound, the first signal is an Amplitude Shift Key (PSK) modulated signal set to a first frequency and the second signal is a single tone signal set to a second frequency.

Embodiment 7

The method according to any of embodiments 1-4, wherein, in order to produce a Hi-Low siren sound, the first signal is a Frequency Shift Key (FSK) modulated signal set to a first frequency and the second signal is a single tone signal set to a second frequency.

Embodiment 8

The method according to any of embodiments 1-4, wherein, in order to emit a verbal message, a verbal message can be modulated by Single Side Band (SSB) modulation technique at the first frequency and the second signal is a single tone signal set to the first frequency.

Embodiment 9

The method according to any of embodiments 1-8, wherein the first signal includes a frequency range and the second signal includes only one frequency.

Embodiment 10

The method according to any of embodiments 1-8, the first signal includes a frequency range and the second signal includes a frequency range.

Embodiment 11

The method according to any of embodiments 1-10, wherein the second signal's emission is delayed, until after the emission of the first signal, by a specific (pre-determined) amount of time.

Embodiment 12

An apparatus for sensorless structural health monitoring, the apparatus comprising:
a first signal generator;
a first actuator (e.g., attached to the first signal generator); and
a second actuator.

Embodiment 13

The apparatus according to embodiment 12, further comprising an amplifier.

Embodiment 14

The apparatus according to any of embodiments 12-13, further comprising a modulator.

Embodiment 15

The apparatus according to any of embodiments 12-14, further comprising a second signal generator (e.g., attached to the second actuator).

Embodiment 16

The apparatus according to any of embodiments 12-15, wherein the apparatus is configured to perform the method according to any of embodiments 1-11.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 4:
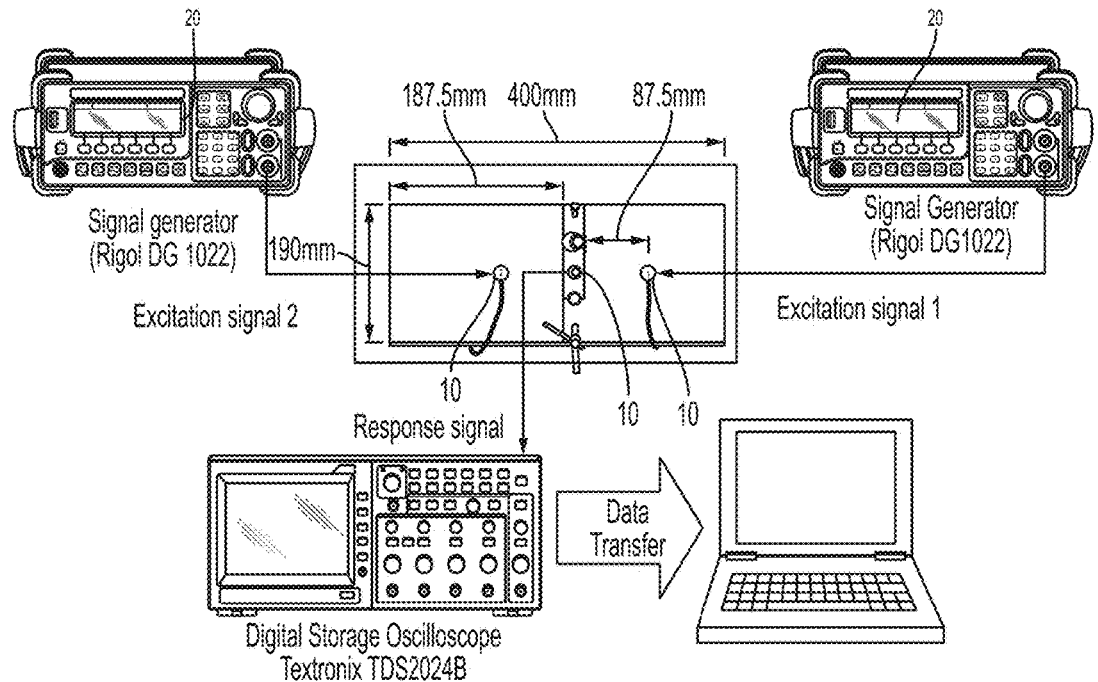
FIG. 4 shows an image of an SHM system.
Figure 5A:
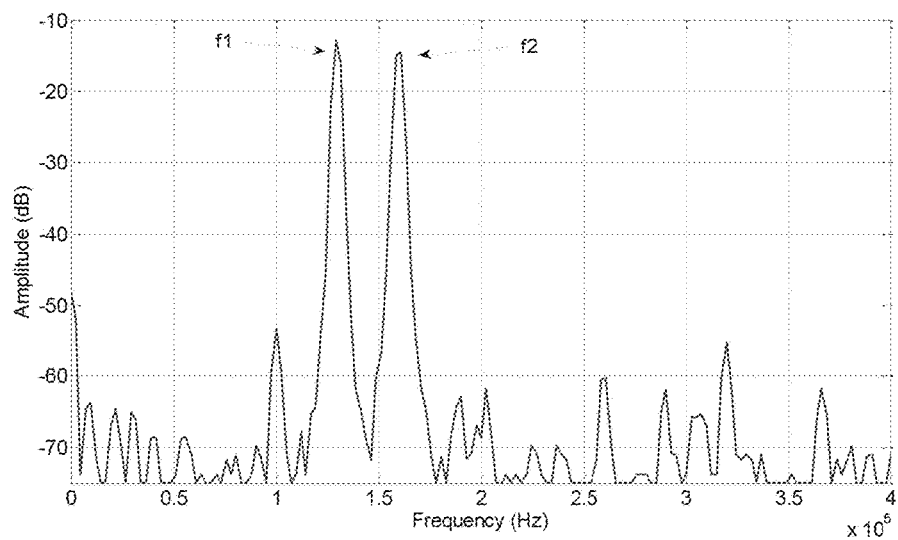
FIGS. 5a and 5b show plots of the frequency spectrum of an output signal for a linear (FIG. 5a) system and nonlinear (FIG. 5b) system.
Figure 5B:
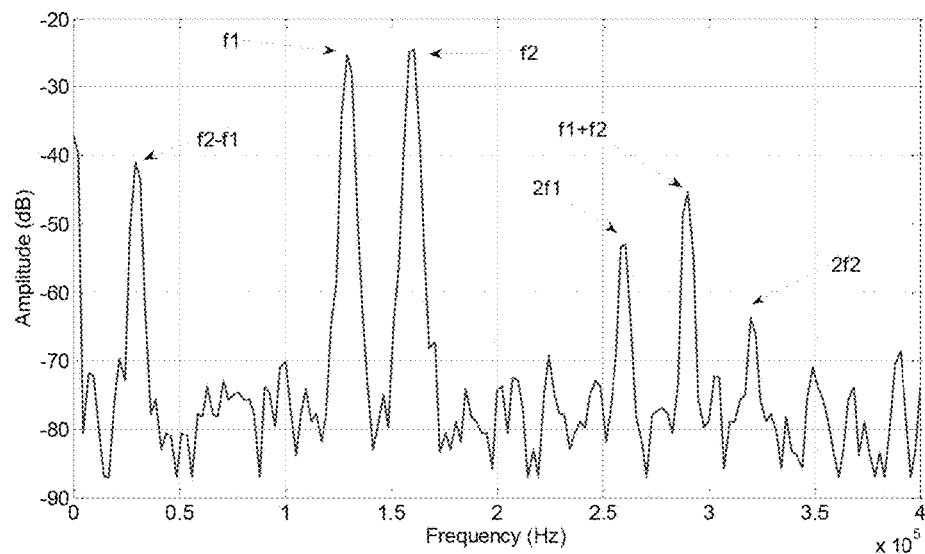

To verify the applicability of the heterodyne effect on an SHM system, the following experiment was conducted. A 200×25×2 mm Al-2024 strip was clamped on top center portion of a second 400×190×2 mm Al-2024 plate. FIG. 4 shows a schematic layout of the experimental set up. In order to excite the structure, two PZT elements were bonded to the larger plate. A third PZT element was bonded to the smaller plate in order to retrieve a response signal. Two Rigol DG1022A arbitrary waveform generators (AWG) were used to generate signals at 130 kHz and 160 kHz, respectively. A Tektronix TDS202 digital oscilloscope retrieved the output signal at a 5 MHz sampling rate. FIG. 5a shows the frequency spectrum of the output response when the plates were clamped together tightly. The spectrogram displays strong signal strength at the original excitation 130 kHz and 160 kHz frequencies. FIG. 5b shows the frequency spectrum of the output response when the clamps are loosened and contact between plate 1 and 2 has diminished. The spectrogram result shows a strong signal strength signals at the original frequencies of 130 kHz, 160 kHz and the new frequencies of 30 kHz and 290 kHz. Therefore, an SHM system can incorporate the heterodyne effect to detect structural defects.

Example 2

Figure 6:
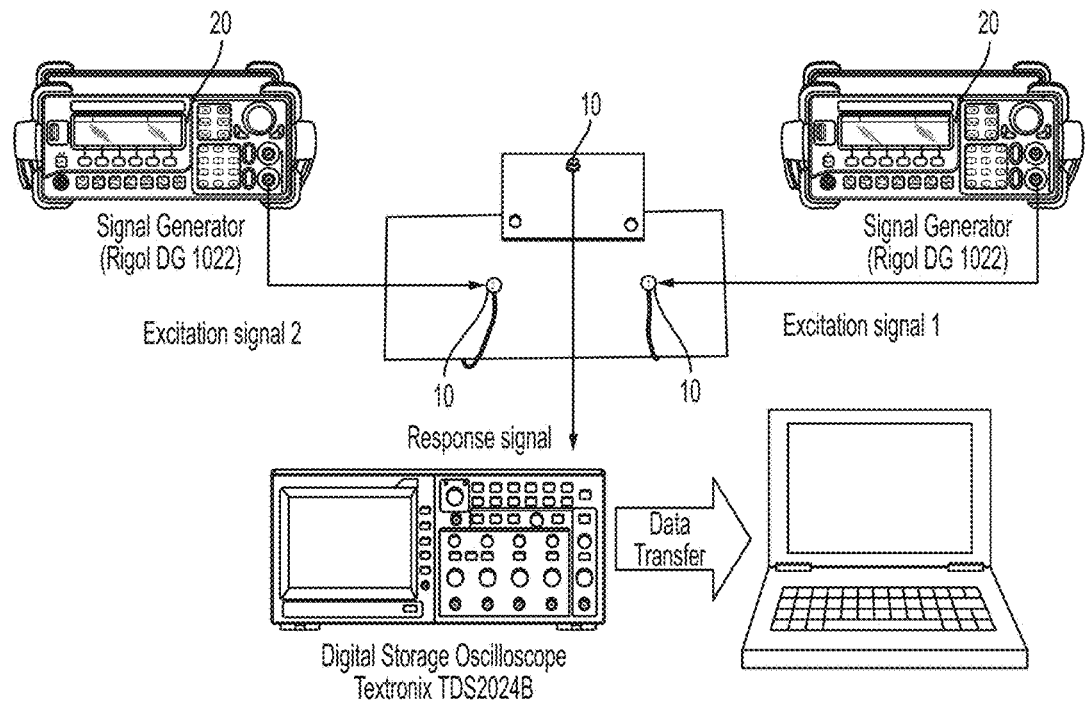
FIG. 6 shows an image of an SHM system.

In order to demonstrate that the heterodyning effect can be used to determine the location of a loose or missing bolt, the following experiment was conducted. FIG. 6 is a schematic view of the experimental set up to locate loose or missing bolts. Two Al-2024 plates were joined with two bolts as shown in FIG. 6. Two PZT elements were connected to the larger plate and a third PZT element was connected to the smaller plate. Two Rigol DG1022 Signal Generators excited the larger plate with a first signal at a first frequency of 140 kHz and a second signal at a second frequency of 170 kHz. The experiment was conducted in the following manner. Initially, the left bolt was removed, the right bolt was tightly bolted in. The first signal's emission was delayed by 50 μs after the emission of the second signal. The signal delay allows the first signal and the second signal to meet across the left bolt location. Then, with the left bolt still removed, the second signal's emission was delayed by 50 μs after the emission of the first signal. The signal delay allows the first signal and the second signal to meet across the right bolt location. The experiment was repeated with the right bolt removed and the left bolt tightly bolted in.

Figure 7A:
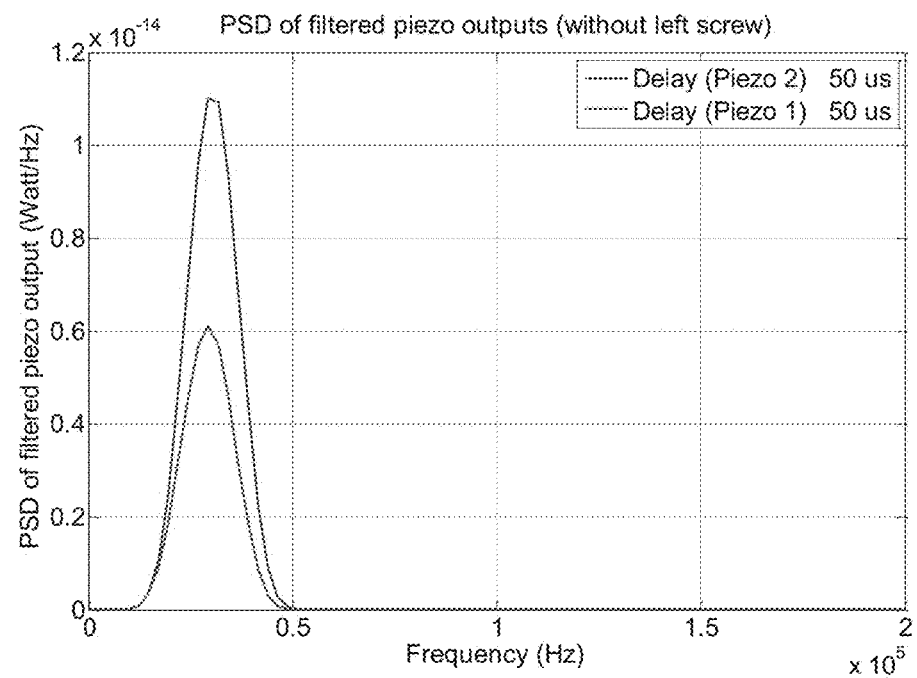
FIGS. 7a and 7b show plots of a power spectral display of output signals of an experiment without a left screw and an experiment without a right screw, respectively.
Figure 7B:
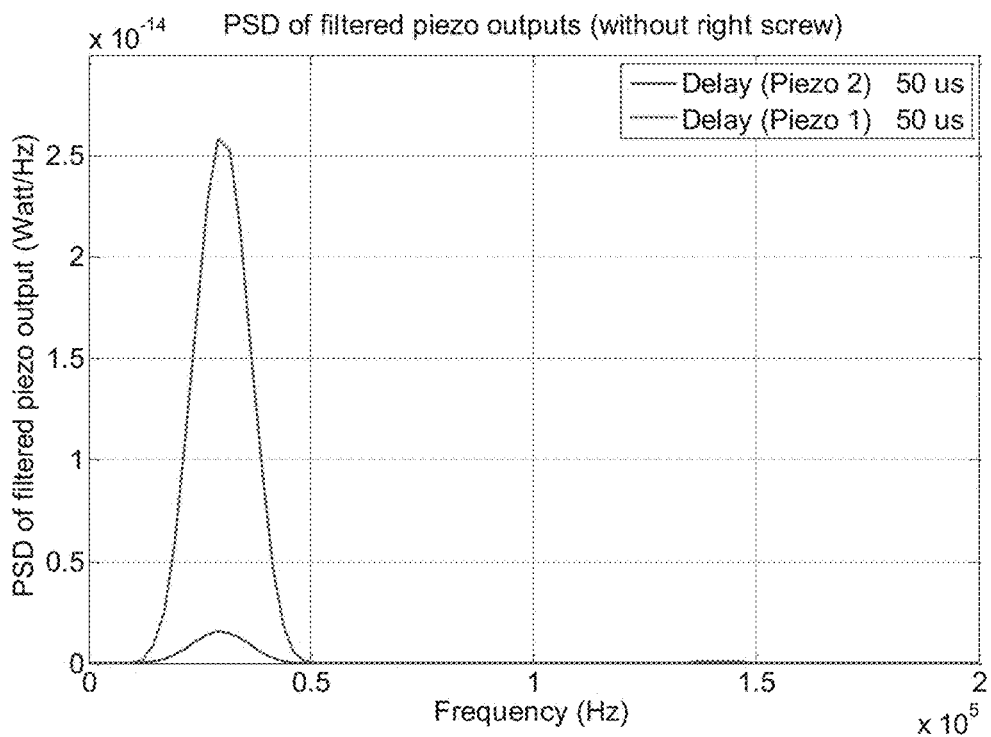

FIG. 7(a) shows the power spectral display of the output response and shows that more signal power is retrieved from the output response when the left bolt is missing and the two signals meet at the location where the left bolt would otherwise be. FIG. 7(b) shows the power spectral display of the output response and that more signal power is present when the right bolt is missing and the signals meet at the location where the right bolt would otherwise be. Therefore, the location of the missing bolt can be determined by an SHM system that incorporates the heterodyne effect.

Example 3

Figure 8:
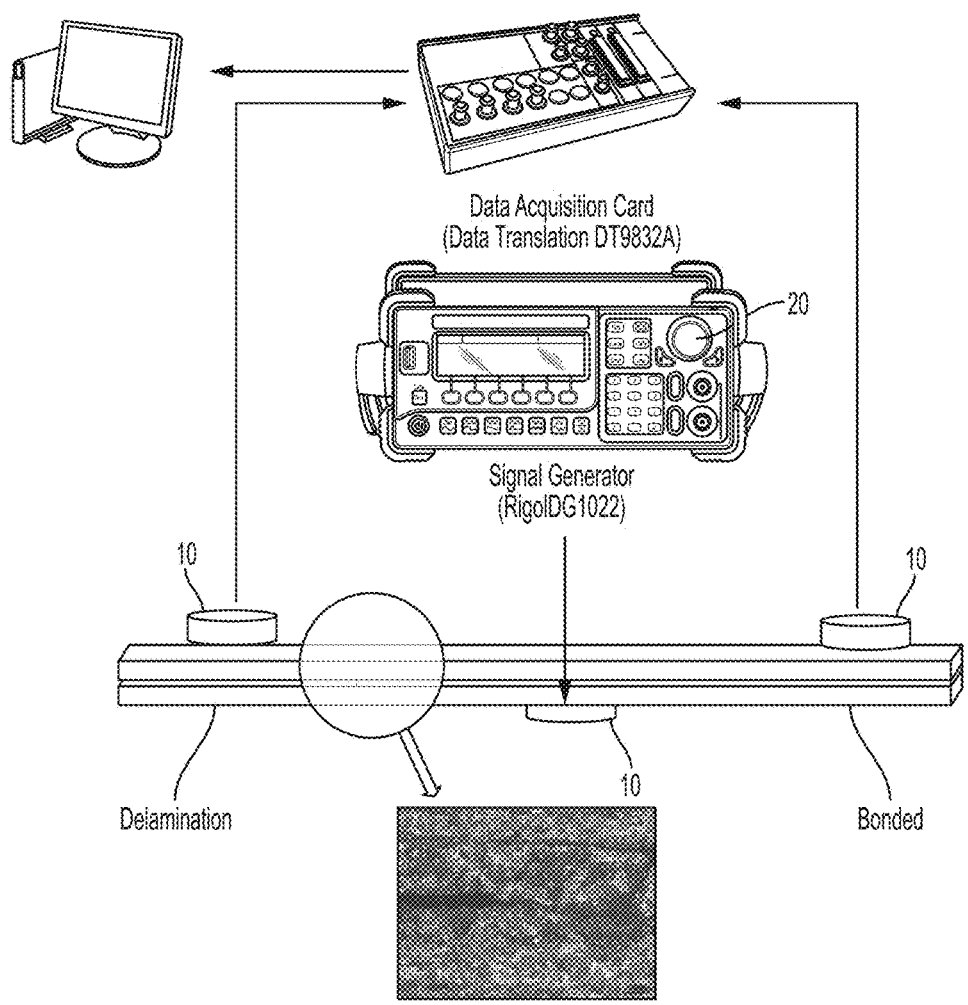
FIG. 8 shows a schematic image of a SHM system.

In order to determine the effectiveness of an SHM that leverages the heterodyne effect in detecting debonding regions, the following experiment was conducted. FIG. 8 is a schematic view of an experimental set up of the SHM system. Two 1"×10" composite coupons were manufactured and bonded together with film adhesive. No adhesive was applied to a 2 inch long region on the left side of the coupon in order to create a region in which debonding could occur. The PZT element located in the middle of the top coupon was excited with a sweep sine wave from 20 kHz to 600 kHz. The signal recovered from the PZT element directly above the debonded region was sampled at 2 MHz, and time frequency analysis was performed using a spectrogram function of MATLAB. The most nonlinear behavior occurred at 300 kHz. The PZT element was then excited with three harmonic signals at 280 kHz, 300 kHz, and 320 kHz. Only signals at 280 kHz, 300 kHz, and 320 kHz were recovered from the PZT element directly over the bonded region. A signal at 20 kHz was recovered from the PZT element directly above the debonded region. The results confirmed that debonded regions can be identified by an SHM system using the heterodyne effect.

Example 4

Figure 9:
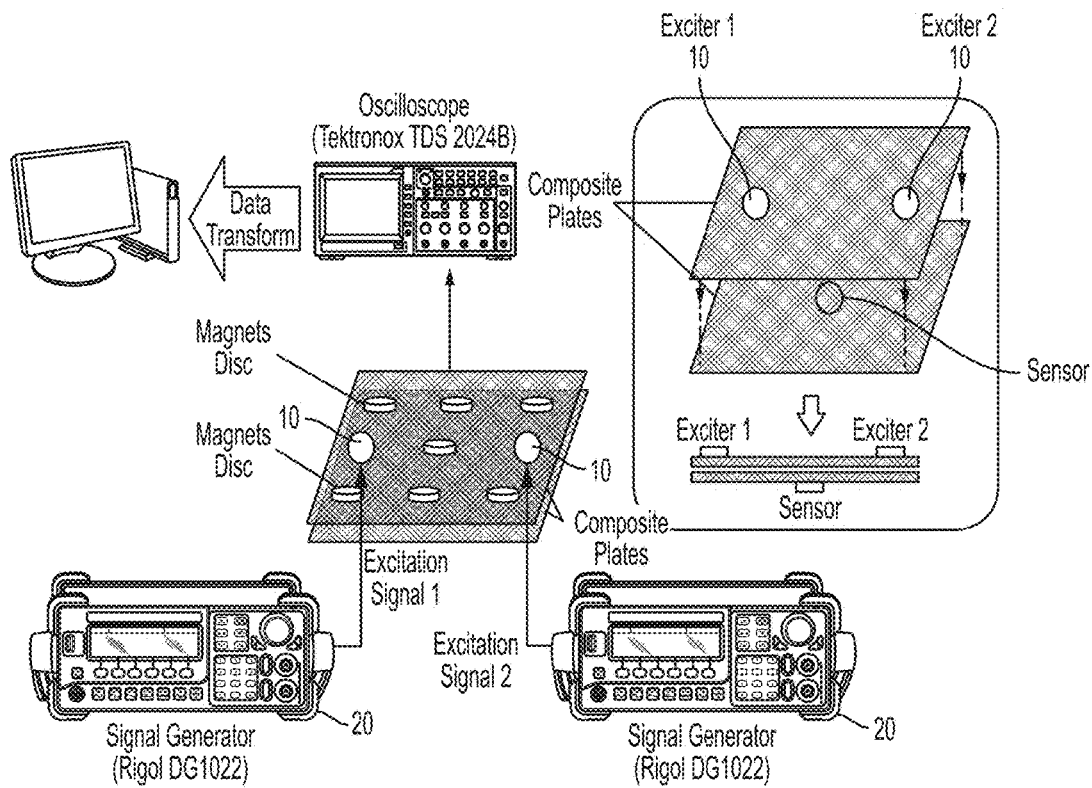
FIG. 9 shows a schematic image of an SHM system.
Figure 10:
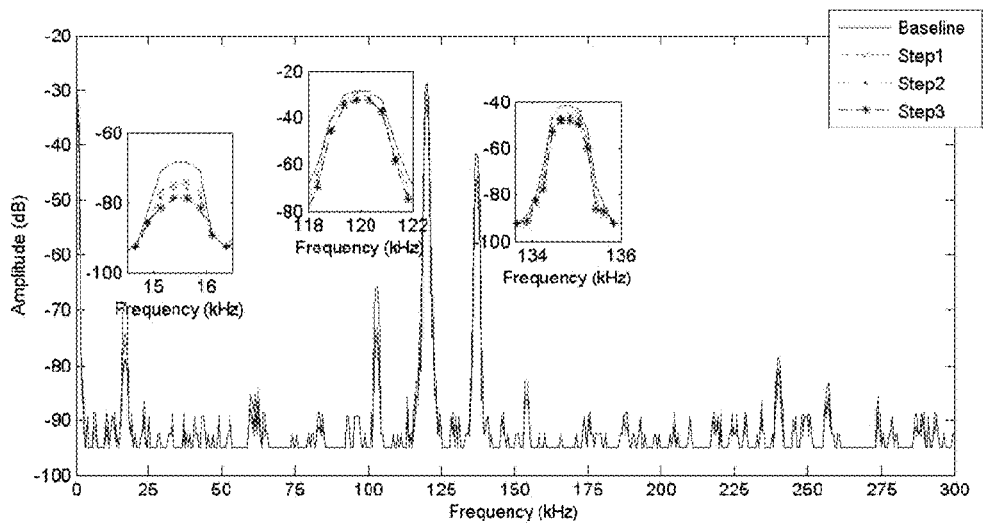
FIG. 10 shows a plot of an output signal of a nonlinear system.

In order to evaluate the relationship between compressive forces applied on the plates and the amplitude of the frequencies contained in an output response, the following experiment was conducted. FIG. 9 is a schematic view of the experimental set up. A composite plate was placed on top of another composite plate. A PZT element located on the top plate was excited with a sweep sine wave from 100 kHz to 300 kHz. The most nonlinear behavior was recorded at 120 kHz and 135 kHz. Then, two PZT elements connected to the top surface of the top composite plate were exited at 120 kHz and 135 kHz respectively. A PZT element connected to the bottom plate sampled the output response at 2 MHz. This experiment was conducted four times with each iteration involving a different amount of compressive force. Initially the compressive force consisted of the weight of the top plate only. The experiment was repeated three times and the plates were held together with 3, 5, and 7 magnets respectively. The results demonstrated that the amplitude of the 15 kHz frequency in the output response, decreased as the compressive forces increased. FIG. 10 show a graph of the spectrums of the signal of sensor at 4 compressive forces. Magnified views of the signals at 15 kHz, 120 kHz, and 135 kHz are provided respectively. The amplitude of the original 120 kHz frequency and 135 kHz frequency remain consistent notwithstanding the increase of compressive forces. However, the 15 kHz frequency contained in the output signal decreases in amplitude as the compressive forces increase or vice versa increases as compressive forces decrease.

Example 5

Figure 11:
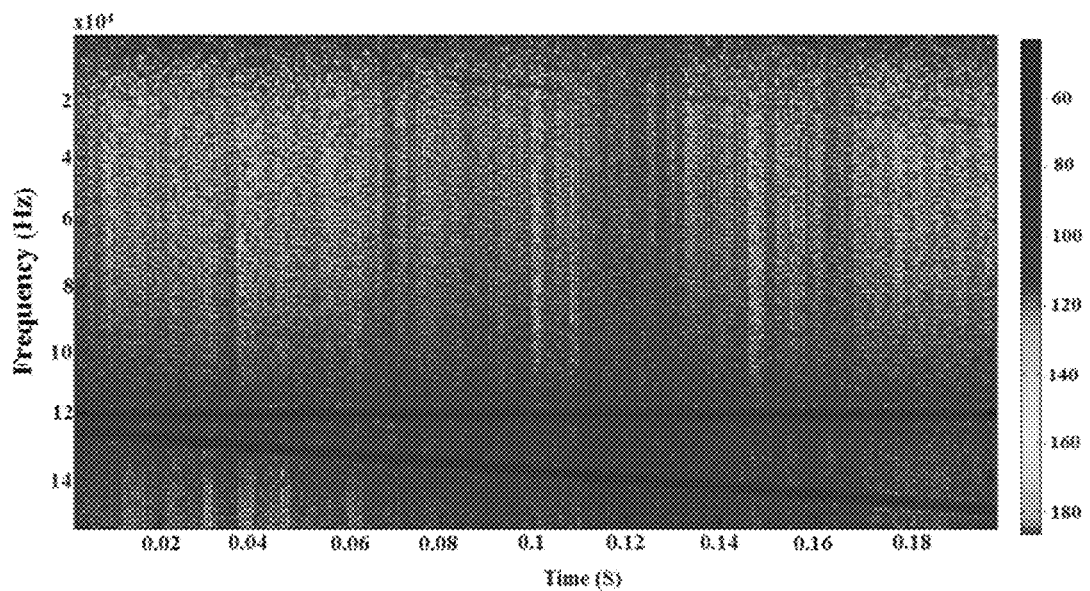
FIG. 11 shows an image of a spectrogram of an output response of an SHM system.

To determine whether an SHM system would accurately detect defects if one actuator was excited with a sweep sine wave rather than set frequency, the following experiment was conducted. A first signal generator was connected to a first PZT element connect to a subject structure containing a structural defect. A second signal generator was connected to a second PZT element connected to the subject structure. The first PZT element was excited at 120 kHz and the second PZT element was excited with a sweep-sine wave from 125 kHz to 150 kHz instead of 135 kHz. Theoretically, a spectrogram of output response should contain line that begins a 5 kHz and continue until 30 kHz. FIG. 11 shows an image of a spectrogram of the output response. FIG. 11 displays a line located on the top of the spectrogram that begins at 5 kHz and continues until 30 kHz. These results indicate that instead of a single frequency, a broad range of frequencies can be used to excite a PZT element.

Example 6

To demonstrate that an SHM system using the heterodyne effect could detect a defect is if both signals consisted of sweep sine waves, the following experiment was conducted. A first signal generator was connected to a first PZT element connected to a structure. A second signal generator was connected to a second PZT element connect to the subject structure. The first PZT element was excited with a descending sweep sine waves of frequencies 350 kHz to 300 kHz. The second PZT element was excited with an ascending sweep sine wave from 200 kHz to 250 kHz. A third PZT element was attached to the subject structure in order to retrieve the output response.

Figure 12A:
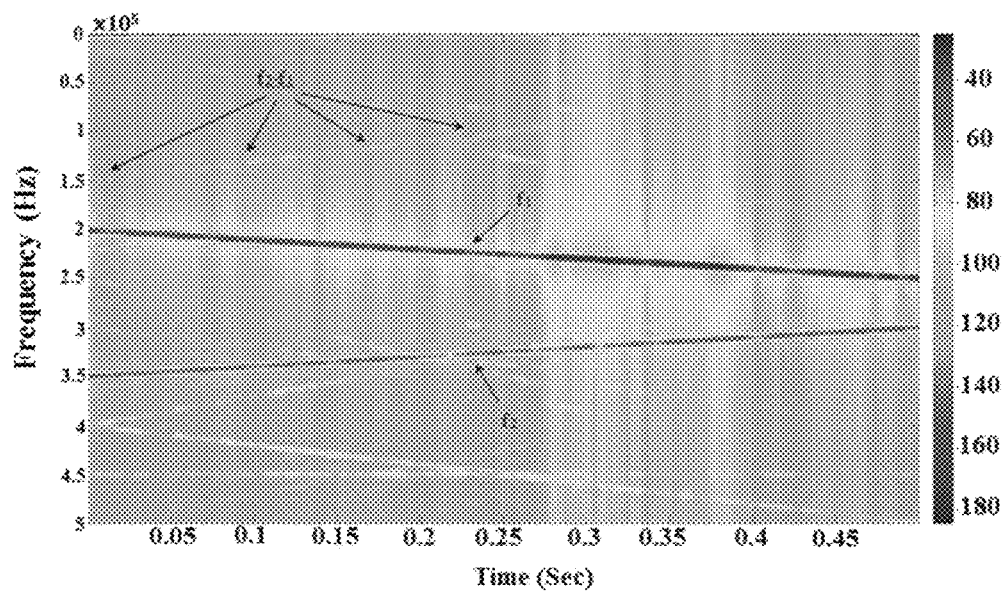
FIGS. 12a and 12b are time-frequency plots of an output response of an SHM system.
Figure 12B:
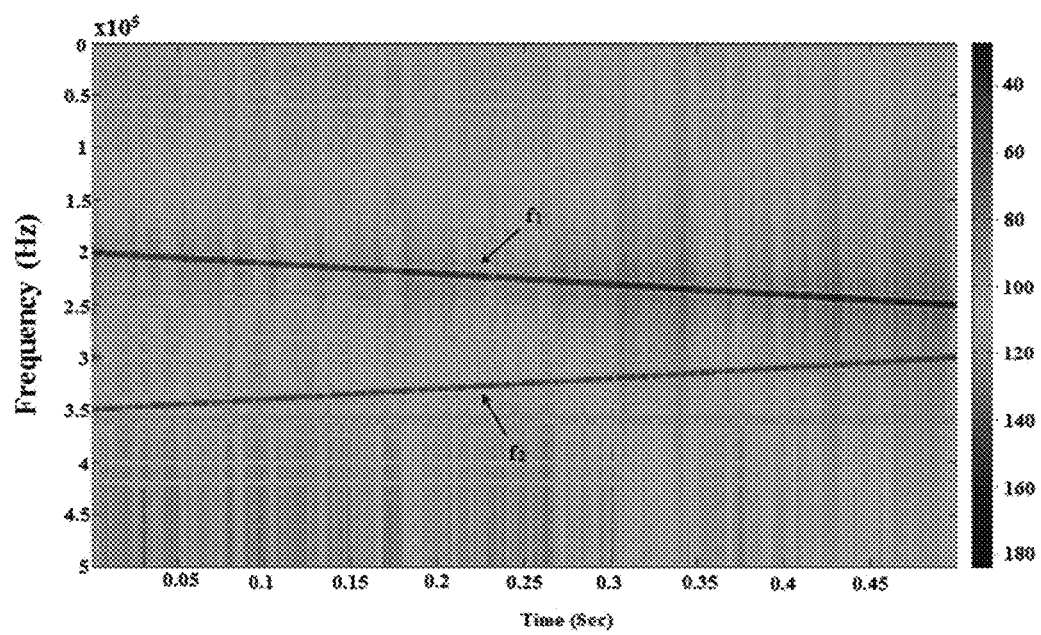

The experiment was conducted using a structure with no structural defects and repeated with a structure containing a defect consisting of a 1 mm crack. FIG. 12 shows a time-frequency plot of the retrieved data. In both plots, the original first excitation sweep sine range (f1) frequencies and second excitation sweep sine range (f2) frequencies present the strongest signals. FIG. 12(a) is the time-frequency plot of the output response when the subject structure included the 1 mm crack. A new frequency range (f2-f1) that consists of the second frequency range subtracted from the first frequency range (f1) is visible near the top of the plot. This new frequency range is created by 1 mm crack acting as a nonlinear mixer, according to the heterodyne effect. FIG. 12(b) is the time-frequency plot of the output response when the subject structure has no structural defects. As no defect to cause the structure to behave as a nonlinear system exists, the plot consists of the first sweep sine wave range (f1) and the second sweep sine frequency range (f2) only.

Example 7

Figure 13:
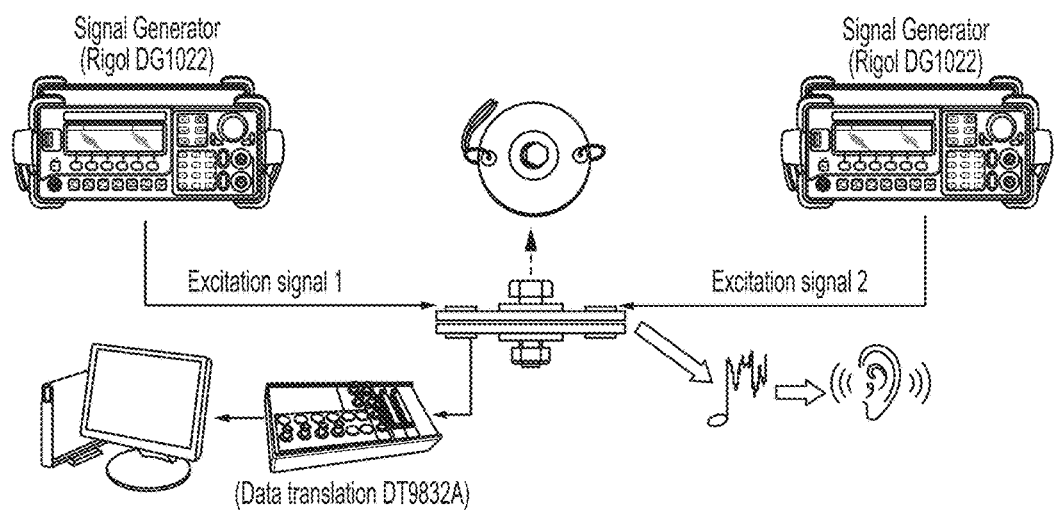
FIG. 13 shows a schematic image of an SHM system.

To demonstrate that an SHM using the heterodyne effect could detect a defect on a bolt like structure, the following experiment was conducted. Two larger washers with outer diameters of 50 mm and two smaller washers with outer diameters of 7 mm were connected by a 25.8 mm long bolt with a diameter of 6.35 mm. The internal diameter of each of the washers was 7.4 mm. FIG. 13 shows a schematic image of the experimental set up. Two PZT actuators were connected to the top surface of the first larger washer. Each of the two PZT actuators was connected to a Rigol DG1022 signal generator respectively. In order to record the signal generated by the system, a third PZT actuator was connected to the bottom surface of the second larger washer.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Buck, O., W. Morris, and J. M. Richardson, Acoustic harmonic generation at unbonded interfaces and fatigue cracks. Applied Physics Letters, 1978. 33(5): p. 371-373.
2. Antonets, V., D. Donskoy, and A. Sutin, Nonlinear vibro-diagnostics of flaws in multilayered structures. Mechanics of Composite Materials, 1986. 15(5): p. 934-937.
3. Donskoy, D., A. Sutin, and A. Ekimov, Nonlinear acoustic interaction on contact interfaces and its use for nondestructive testing. NDT & E International, 2001. 34(4): p. 231-238.
4. Jiao, J., et al., ChinaContact defect detection in plates using guided wave and vibro-acoustic modulation.
5. Dziedziech, K., et al., Enhanced nonlinear crack-wave interactions for structural damage detection based on guided ultrasonic waves. Structural Control and Health Monitoring, 2016.
6. Zaitsev, V., et al., Novel nonlinear-modulation acoustic technique for crack detection. NDT & E International, 2006. 39(3): p. 184-194.
7. Cooper, C., Physics. 2001: Taylor & Francis.
8. Graf, R. F., Modern dictionary of electronics. 1999: Newnes.
9. Verbiest, G. and M. Rost, Beating beats mixing in heterodyne detection schemes. Nature communications, 2015. 6.
10. Hitchman, S., et al., Heterodyne interferometry for the detection of elastic waves: a tutorial and open-hardware project. European Journal of Physics, 2015. 36(3): p. 035011.
11. McElroy, J. H., Infrared heterodyne solar radiometry. Applied optics, 1972. 11(7): p. 1619-1622.
12. Okoshi, T., Recent advances in coherent optical fiber communication systems. Lightwave Technology, Journal of, 1987. 5(1): p. 44-52.

13. Ludlow, A. D., et al., Optical atomic clocks. Reviews of Modern Physics, 2015. 87(2): p. 637.
14. Stolarczyk, L. G., et al., Acoustic heterodyne radar. 2014, Google Patents.
15. Pure, S. and J. D. Wallace, Underwater acoustic navigation system. 1969, Google Patents.
16. K. Geren, M. Papineau, and C. Routh, "Heterodyne autocorrelation guidance system," U.S. Pat. No. 3,836,951, 1974.
17. Croft, J. J. and E. G. Norris, Parametric virtual speaker and surround-sound system. 2004, Google Patents.
18. Norris, E. G., Directable sound and light toy. 1999, Google Patents.
19. Bostick, J. H., et al., Pressure and frequency modulated non-lethal acoustic weapon. 2011, Google Patents.
20. Naff, J. T. and J. H. Shea, Acoustic cannon. 1999.
21. Junker, G. H., New criteria for self-loosening of fasteners under vibration. 1969, SAE Technical Paper.
22. Sauer, J., D. Lemmon, and E. Lynn, Bolts: how to prevent their loosening. Mechanical Design, 1950. 22: p. 133-139.
23. SAKAI, T., Investigations of Bolt Loosening Mechanisms: 1st Report, On the Bolts of Transversely Loaded Joints. Bulletin of JSME, 1978. 21(159): p. 1385-1390.
24. Su, Z., L. Ye, and Y. Lu, Guided Lamb waves for identification of damage in composite structures: A review. Journal of sound and vibration, 2006. 295(3): p. 753-780.
25. Raghavan, A. and C. E. Cesnik, Review of guided-wave structural health monitoring. Shock and Vibration Digest, 2007. 39(2): p. 91-116.
26. Demetgul, M., et al., Evaluation of the health of riveted joints with active and passive structural health monitoring techniques. Measurement, 2015. 69: p. 42-51.
27. Yan, W. and W. Chen, Structural health monitoring using high-frequency electromechanical impedance signatures. Advances in Civil Engineering, 2010. 2010.
28. Annamdas, V. G. and M. A. Radhika, Electromechanical impedance of piezoelectric transducers for monitoring metallic and non-metallic structures: A review of wired, wireless and energy-harvesting methods. Journal of Intelligent Material Systems and Structures, 2013: p. 1045389X13481254.
29. Chakraborty, D., et al., Damage classification structural health monitoring in bolted structures using time-frequency techniques. Journal of Intelligent Material Systems and Structures, 2009
30. Tansel, I. N., et al. Monitoring the integrity of machine assemblies by using surface response to excitation (SuRE) approach. in Recent Advances in Space Technologies (RAST), 2011 5th International Conference on. 2011. IEEE.
31. Galrmandi, H., et al., Inspection of the integrity of a multi-bolt robotic arm using a scanning laser vibrometer and implementing the Surface Response to Excitation Method (SuRE). International Journal of Prognostics and Health Management, 2014. 5(1): p. 1-10.
32. Kessler, S. S., S. M. Spearing, and C. Soutis, Damage detection in composite materials using Lamb wave methods. Smart Materials and Structures, 2002. 11(2): p. 269.
33. Larson, B., NDT Education Resource Center Developed by the Collaboration for NDT Education. Center for Nondestructive Evaluation, Iowa State University, Ames, Iowa, 2001. 50011.
34. V. Y. Senyurek, "Detection of cuts and impact damage at the aircraft wing slat by using Lamb wave method," Measurement, vol. 67, pp. 10-23, 5/2015.
35. H. Fekrmandi, M. Unal, A. Baghalian, S. Tashakori, K. Oyola, A. Alsenawi, et al., "A non-contact method for part-based process performance monitoring in end milling operations," The International Journal of Advanced Manufacturing Technology, pp. 1-8, 2015.
36. G. H. Junker, "New criteria for self-loosening of fasteners under vibration," SAE Technical Paper 0148-7191, 1969.
37. W. Yan and W. Chen, "Structural health monitoring using high-frequency electromechanical impedance signatures," Advances in Civil Engineering, vol. 2010, 2010.
38. V. Giurgiutiu, Structural health monitoring: with piezoelectric wafer active sensors: Academic Press, 2007.
39. F. Wu, H.-L. Chan, and F.-K. Chang, "Ultrasonic guided wave active sensing for monitoring of split failures in reinforced concrete," Structural Health Monitoring, p. 1475921715591876, 2015.
40. C. E. Cooper, Physics: Fitzroy Dearborn, 2001.
41. U. S. B. o. N. Personnel, Basic Electronics: Courier Dover, 1973. fekrimand
42. V. Giurgiutiu, A. Zagrai, and J. Jing Bao, "Piezoelectric Wafer Embedded Active Sensors for Aging Aircraft Structural Health Monitoring," Struct. Heal. Monit., vol. 1, no. 1, pp. 41-61, 2002.
43. W. J. Victorewski, S. Mahzan, and R. Traynor, "Health monitoring of aerospace composite structures—Active and passive approach," Compos. Sci. Technol., vol. 69, no. 11-12, pp. 1678-1685, 2009.
44. G. Victor, "Structural health monitoring with piezoelectric wafer active sensors—predictive modeling and simulation," Incas Bull., vol. 2, no. 3, pp. 31-44, 2010.
45. B. S. Ben, B. a. Ben, K. a. Vikram, and S. H. Yang, "Damage identification in composite materials using ultrasonic based Lamb wave method," Measurement, vol. 46, no. 2, pp. 904-912, 2013.
46. M. Carboni, A. Gianneo, and M. Giglio, "A Lamb waves based statistical approach to structural health monitoring of carbon fibre reinforced polymer composites," Ultrasonics, vol. 60, pp. 51-64, 2015.
47. K. Diamanti and C. Soutis, "Structural health monitoring techniques for aircraft composite structures," Prog. Aerosp. Sci., vol. 46, no. 8, pp. 342-352, 2010.
48. F. Li, Z. Liu, X. Sun, H. Li, and G. Meng, "gation of guided waves in pressure vessel," Wave Motion, vol. 52, pp. 216-228, 2015.
49. K. Liu, Z. Wu, Y. Jiang, Y. Wang, K. Zhou, and Y. Chen, "Guided waves based diagnostic imaging of circumferential cracks in small-diameter pipe," Ultrasonics, vol. 65, pp. 34-42, 2016.
50. R. Carandente and P. Cawley, "The effect of complex defect profiles on the reflection of the fundamental torsional mode in pipes," NDT E Int., vol. 46, no. 1, pp. 41-47, 2012.
51. A. Galvagni and P. Cawley, "The reflection of guided waves from simple support in pipes," J. Acoust. Soc. . . . , vol. 129, no. September, pp. 1869-1880, 2011.
52. Z. Liu, C. He, B. Wu, X. Wang, and S. Yang, "Circumferential and longitudinal defect detection using T(0, 1) mode excited by thickness shear mode piezoelectric elements," Ultrasonics, vol. 44, no. SUPPL., pp. 1135-1138, 2006.
53. S. Ma, Z. Wu, Y. Wang, and K. Liu, "The reflection of guided waves from simple dents in pipes," Ultrasonics, vol. 57, no. C, pp. 190-197, 2015.

54. M. Ratassepp, S. Fletcher, and M. J. S. Lowe, "Scattering of the fundamental torsional mode at an axial crack in a pipe.," J. Acoust. Soc. Am., vol. 127, no. 2, pp. 730-740, 2010.
55. D. K. Stoyko, N. Popplewell, and A. H. Shah, "Detecting and describing a notch in a pipe using singularities," Int. J. Solids Struct., vol. 51, no. 15-16, pp. 2729-2743, 2014.
56. H. Fekrimandi, I. Nur Tansel, R. Gonzalez, S. Rojas, D. Meiller, K. Lindsay, A. Baghalian, and S. Tashakori, "Implementation of the Surface Response to Excitation (SuRE) Method with DSP's for Detection of the Damage of Thick Blocks," in Structural Health Monitoring 2015, 2015.
57. H. Fekrmandi, J. Rojas, I. N. Tansel, A. Yapici, and B. Uragun, "Investigation of the computational efficiency and validity of the surface response to excitation method," Meas. J. Int. Meas. Confed., vol. 62, pp. 33-40, 2015.
58. H. Fekrmandi, M. Unal, A. Baghalian, S. Tashakori, K. Oyola, A. Alsenawi, and I. N. Tansel, "A non-contact method for part-based process performance monitoring in end milling operations," Int. J. Adv. Manuf. Technol., pp. 13-20, 2015.
59. V. Giurgiutiu and A. Zagrai, "Electro-mechanical impedance method for crack detection in metallic plates," Proc. SPIE—Int. Soc. Opt. Eng., vol. 4335, no. October, pp. 131-142, 2001.
60. S. R. Hamzeloo, M. Shamshirsaz, and S. M. Rezaei, "Damage detection on hollow cylinders by Electro-Mechanical Impedance method: Experiments and Finite Element Modeling," Comptes Rendus—Mec., vol. 340, no. 9, pp. 668-677, 2012.
61. J. Min, S. Park, C. B. Yun, C. G. Lee, and C. Lee, "Impedance-based structural health monitoring incorporating neural network technique for identification of damage type and severity," Eng. Struct., vol. 39, pp. 210-220, 2012.
62. G. Park, H. H. Cudney, and D. J. Inman, "Feasibility of using impedance-based damage assessment for pipeline structures," Earthq. Eng. Struct. Dyn., vol. 30, no. 10, pp. 1463-1474, 2001.
63. S. Tashakori, A. Baghalian, M. Unal, H. Fekrmandi, volkan y senyürek, D. McDaniel, and I. N. Tansel, "Contact and non-contact approaches in load monitoring applications using surface response to excitation method," Measurement, vol. 89, pp. 197-203, 2016.
64. B. Xu and V. Giurgiutiu, "Single mode tuning effects on lamb wave time reversal with piezoelectric wafer active sensors for structural health monitoring," J. Nondestruct. Eval., vol. 26, no. 2-4, pp. 123-134, 2007.
65. C. H. Wang, J. T. Rose, and F.-K. Chang, "A synthetic time-reversal imaging method for van denstructural health monitoring," Smart Mater. Struct., vol. 13, no. 2, pp. 415-423, 2004.
66. T. Leutenegger and J. Dual, "Non-destructive testing of tubes using a time reverse numerical simulation (TRNS) method," Ultrasonics, vol. 41, no. 10, pp. 811-822, 2004.
67. X. Guo, D. Zhang, and J. Zhang, "Detection of fatigue-induced micro-cracks in a pipe by using time-reversed nonlinear guided waves: A three-dimensional model study," Ultrasonics, vol. 52, no. 7, pp. 912-919, 2012.
68. M. Meo and G. Zumpano, "Nonlinear elastic wave spectroscopy identification of impact damage on a sandwich plate," Compos. Struct., vol. 71, no. 3-4, pp. 469-474, 2005.
99. M. Meo, U. Polimeno, and G. Zumpano, "Detecting damage in composite material using nonlinear elastic wave spectroscopy methods," Appl. Compos. Mater., vol. 15, no. 3, pp. 115-126, 2008.
70. K. E.-a. Van Den Abeele, P. a. Johnson, and A. Sutin, "Nonlinear Elastic Wave Spectroscopy (NEWS) Techniques to Discern Material Damage, Part II: Single-Mode Nonlinear Resonance Acoustic Spectroscopy," Res. Nondestruct. Eval., vol. 12, no. 1, pp. 17-30, 2000.
71. P. A. Johnson and A. Sutin, "Nonlinear elastic wave NDE I. Nonlinear resonant ultrasound spectroscopy and slow dynamics diagnostics," AIP Conf. Proc., vol. 760, pp. 377-384, 2005.
72. X. Liu, Z. Dao, J. Zhu, W. Qu, X. Gong, K. Van Den Abeele, and L. Ma, "Localization of material defects using nonlinear resonant ultrasound spectroscopy under asymmetric boundary conditions," Phys. Procedia, vol. 3, no. 1, pp. 55-61, 2010.
73. K. Van Den Abeele, "Multi-mode nonlinear resonance ultrasound spectroscopy for defect imaging: an analytical approach for the one-dimensional case.," J. Acoust. Soc. Am., vol. 122, no. 1, pp. 73-90, 2007.
74. N. Houhat and V. Tournat, "One-dimensional Parametric Study of Damage Detection in a Solid Material using a Nonlinear Wave Modulation Spectroscopy (NWMS) Technique," no. Icee, pp. 1-4, 2015.
75. P. Liu, H. Sohn, T. Kundu, and S. Yang, "Noncontact detection of fatigue cracks by laser nonlinear wave modulation spectroscopy (LNWMS)," NDT E Int., vol. 66, pp. 106-116, 2014.
76. L. Straka, Y. Yagodzinskyy, M. Landa, and H. Hänninen, "Detection of structural damage of aluminum alloy 6082 using elastic wave modulation spectroscopy," NDT E Int., vol. 41, no. 7, pp. 554-563, 2008.
77. Fessenden, Reginald A. "Height indicator." U.S. Pat. No. 1,991,892. 19 Feb. 1935.
78. T.-C. Poon, "DETECTION|Heterodyning," in Encyclopedia of Modern Optics, 2005, pp. 201-206.
79. E. Norris, "Acoustic heterodyne device and method," U.S. Pat. No. 5,889,870, 1999.
80. D. Gabor, "Theory of communication. Part 1: The analysis of information," Electr. Eng.—Part III Radio Commun. Eng. J. Inst., vol. 93, no. 26, pp. 429-441, 1946.
81. M. Demetgul, V. Y. Senyurek, R. Uyandik, I. N. Tansel, and O. Yazicioglu, "Evaluation of the health of riveted joints with active and passive structural health monitoring techniques," Measurement, vol. 69, pp. 42-51, 2015.
82. W. J. Staszewski, S. Mahzan, and R. Traynor, "Health monitoring of aerospace composite structures—Active and passive approach," Compos. Sci. Technol., vol. 69, no. 11-12, pp. 1678-1685, 2009.
83. G. Victor, "Structural health monitoring with piezoelectric wafer active sensors—predictive modeling and simulation," Incas Bull., vol. 2, no. 3, pp. 31-44, 2010.
84. V. Giurgiutiu, A. Zagrai, and J. Jing Bao, "Piezoelectric Wafer Embedded Active Sensors for Aging Aircraft Structural Health Monitoring," Struct. Heal. Monit., vol. 1, no. 1, pp. 41-61, 2002.
85. H. Fekrmandi, M. Unal, A. Baghalian, S. Tashakori, K. Oyola, A. Alsenawi, and I. N. Tansel, "A non-contact method for part-based process performance monitoring in end milling operations," Int. J. Adv. Manuf. Technol., pp. 13-20, 2015.
86. H. Fekrmandi, M. Unal, S. Rojas Neva, I. N. Tansel, and D. McDaniel, "A novel approach for classification of loads on plate structures using artificial neural networks," Measurement, vol. 82, pp. 37-45, 2016.
87. S. Tashakori, A. Baghalian, M. Unal, H. Fekrmandi, volkan y senyürek, D. McDaniel, and I. N. Tansel, "Contact and non-contact approaches in load monitoring applications using surface response to excitation method," Measurement, vol. 89, pp. 197-203, 2016.
88. H. Fekrmandi, J. Rojas, I. N. Tansel, A. Yapici, and B. Uragun, "Investigation of the computational efficiency and validity of the surface response to excitation method," Meas. J. Int. Meas. Confed., vol. 62, pp. 33-40, 2015.
89. H. Fekrmandi, J. Rojas, J. Campbell, I. N. Tansel, B. Kaya, S. Taskin, and E. Engineering, "Inspection of the Integrity of a Multi-Bolt Robotic Arm Using a Scanning Laser Vibrometer and Implementing the Surface Response to Excitation Method (SuRE)," pp. 1-10, 2014.
90. V. Giurgiutiu and A. Zagrai, "Electro-mechanical impedance method for crack detection in metallic plates," Proc. SPIE—Int. Soc. Opt. Eng., vol. 4335, no. October, pp. 131-142, 2001.
91. G. Park, H. H. Cudney, and D. J. Inman, "Feasibility of using impedance-based damage assessment for pipeline structures," Earthq. Eng. Struct. Dyn., vol. 30, no. 10, pp. 1463-1474, 2001.
92. J. Min, S. Park, C. B. Yun, C. G. Lee, and C. Lee, "Impedance-based structural health monitoring incorporating neural network technique for identification of damage type and severity," Eng. Struct., vol. 39, pp. 210-220, 2012.
93. S. R. Hamzeloo, M. Shamshirsaz, and S. M. Rezaei, "Damage detection on hollow cylinders by Electro-Mechanical Impedance method: Experiments and Finite Element Modeling," Comptes Rendus—Mec., vol. 340, no. 9, pp. 668-677, 2012.
94. H. Fekrmandi, R. Gonzalez, S. Rojas, I. N. Tansel, D. Meiller, and K. Lindsay, "Excitation (SuRE) Method by using Neural Networks," vol. 3420, pp. 11-16, 2015.
95. a Galvagni and P. Cawley, "The reflection of guided waves from simple support in pipes," J. Acoust. Soc. . . . , vol. 129, no. September, pp. 1869-1880, 2011.
96. D. N. Alleyne and P. Cawley, "The excitation of Lamb waves in pipes using dry-coupled piezoelectric transducers," J. Nondestruct. Eval., vol. 15, no. 1, pp. 11-20, 1996.
97. S. Ma, Z. Wu, Y. Wang, and K. Liu, "The reflection of guided waves from simple dents in pipes," Ultrasonics, vol. 57, no. C, pp. 190-197, 2015.
98. D. K. Stoyko, N. Popplewell, and A. H. Shah, "Detecting and describing a notch in a pipe using singularities," Int. J. Solids Struct., vol. 51, no. 15-16, pp. 2729-2743, 2014.
99. Z. Liu, C. He, B. Wu, X. Wang, and S. Yang, "Circumferential and longitudinal defect detection using T(0, 1) mode excited by thickness shear mode piezoelectric elements," Ultrasonics, vol. 44, no. SUPPL., pp. 1135-1138, 2006.
100. M. H. S. Siqueira, C. E. N. Gatts, R. R. Da Silva, and J. M. A. Rebello, "The use of ultrasonic guided waves and wavelets analysis in pipe inspection," Ultrasonics, vol. 41, no. 10, pp. 785-797, 2004.
101. M. Ratassepp, S. Fletcher, and M. J. S. Lowe, "Scattering of the fundamental torsional mode at an axial crack in a pipe.," J. Acoust. Soc. Am., vol. 127, no. 2, pp. 730-740, 2010.
102. R. Carandente and P. Cawley, "The effect of complex defect profiles on the reflection of the fundamental torsional mode in pipes," NDT E Int., vol. 46, no. 1, pp. 41-47, 2012.
103. R. Ahmad and T. Kundu, "Structural health monitoring of steel pipes under different boundary conditions and choice of signal processing techniques," Adv. Civ. Eng., vol. 2012, 2012.
104. F. Li, Z. Liu, X. Sun, H. Li, and G. Meng, "Propagation of guided waves in pressure vessel," Wave Motion, vol. 52, pp. 216-228, 2015.
105. T. Wang, C. Yang, L. Ye, D. Spray, and Y. Xiang, "Evaluation of guided wave propagation in steel pipes," Recent Adv. Struct. Integr. Anal.—Proc. Int. Congr., pp. 255-260, 2014.
106. H. W. Kim, H. J. Lee, and Y. Y. Kim, "Health monitoring of axially-cracked pipes by using helically propagating shear-horizontal waves," NDT E Int., vol. 46, no. 1, pp. 115-121, 2012.
107. W. Zhou, F. G. Yuan, and T. Shi, "Guided torsional wave generation of a linear in-plane shear piezoelectric array in metallic pipes," Ultrasonics, vol. 65, pp. 69-77, 2016.
108. K. Diamanti and C. Soutis, "Structural health monitoring techniques for aircraft composite structures," Prog. Aerosp. Sci., vol. 46, no. 8, pp. 342-352, 2010.
109. M. Carboni, A. Gianneo, and M. Giglio, "A Lamb waves based statistical approach to structural health monitoring of carbon fibre reinforced polymer composites," Ultrasonics, vol. 60, pp. 51-64, 2015.
110. B. S. Ben, B. a. Ben, K. a. Vikram, and S. H. Yang, "Damage identification in composite materials using ultrasonic based Lamb wave method," Measurement, vol. 46, no. 2, pp. 904-912, 2013.
111. J.-H. Lee and S.-J. Lee, "Application of laser-generated guided wave for evaluation of corrosion in carbon steel pipe," NDT E Int., vol. 42, no. 3, pp. 222-227, 2009.
112. K. Liu, Z. Wu, Y. Jiang, Y. Wang, K. Zhou, and Y. Chen, "Guided waves based diagnostic imaging of circumferential cracks in small-diameter pipe," Ultrasonics, vol. 65, pp. 34-42, 2016.
113. A. Baltazar, E. Rojas, and R. Mijarez, "Structural Health Monitoring in Cylindrical Structures Using Helical Guided Wave Propagation," Phys. Procedia, vol. 70, pp. 686-689, 2015.
114. B. Xu and V. Giurgiutiu, "Single mode tuning effects on lamb wave time reversal with piezoelectric wafer active sensors for structural health monitoring," J. Nondestruct. Eval., vol. 26, no. 2-4, pp. 123-134, 2007.
115. B. Wu, "A Time-Reversal Defect—Identifying Method for Guided Wave Inspection in Pipes," vol. 130, no. May, pp. 1-8, 2008.
116. C. H. Wang, J. T. Rose, and F.-K. Chang, "A synthetic time-reversal imaging method for structural health monitoring," Smart Mater. Struct., vol. 13, no. 2, pp. 415-423, 2004.
117. Y. Jin, D. Zhao, and Y. Ying, "<title>Time reversal data communications on pipes using guided elastic waves: Part I. Basic principles</title>," vol. 7984, no. 410, p. 79840B-79840B-12, 2011.
118. T. Leutenegger and J. Dual, "Non-destructive testing of tubes using a time reverse numerical simulation (TRNS) method," Ultrasonics, vol. 41, no. 10, pp. 811-822, 2004.
119. X. Guo, D. Zhang, and J. Zhang, "Detection of fatigue-induced micro-cracks in a pipe by using time-reversed nonlinear guided waves: A three-dimensional model study," Ultrasonics, vol. 52, no. 7, pp. 912-919, 2012.
120. T. Leutenegger, "Detection of defects in cylindrical structures using a time reverse numerical simulation method," vol. 40, pp. 721-725, 2002.
121. K. E.-a. Van Den Abeele, P. a. Johnson, and A. Sutin, "Nonlinear Elastic Wave Spectroscopy (NEWS) Techniques to Discern Material Damage, Part II: Single-Mode Nonlinear Resonance Acoustic Spectroscopy," Res. Nondestruct. Eval., vol. 12, no. 1, pp. 17-30, 2000.

122. G. Zumpano and M. Meo, "Damage detection in an aircraft foam sandwich panel using nonlinear elastic wave spectroscopy," Comput. Struct., vol. 86, no. 3-5, pp. 483-490, 2008.
123. G. Zumpano and M. Meo, "Damage localization using transient non-linear elastic wave spectroscopy on composite structures," Int. J. Non. Linear. Mech., vol. 43, no. 3, pp. 217-230, 2008.
124. M. Meo, U. Polimeno, and G. Zumpano, "Detecting damage in composite material using nonlinear elastic wave spectroscopy methods," Appl. Compos. Mater., vol. 15, no. 3, pp. 115-126, 2008.
125. M. Meo and G. Zumpano, "Nonlinear elastic wave spectroscopy identification of impact damage on a sandwich plate," Compos. Struct., vol. 71, no. 3-4, pp. 469-474, 2005.
126. U. Polimeno and M. Meo, "Understanding the effect of boundary conditions on damage identification process when using non-linear elastic wave spectroscopy methods," Int. J. Non. Linear. Mech., vol. 43, no. 3, pp. 187-193, 2008.
127. K. Van Den Abeele, "Multi-mode nonlinear resonance ultrasound spectroscopy for defect imaging: an analytical approach for the one-dimensional case.," J. Acoust. Soc. Am., vol. 122, no. 1, pp. 73-90, 2007.
128. P. A. Johnson and A. Sutin, "Nonlinear elastic wave NDE I. Nonlinear resonant ultrasound spectroscopy and slow dynamics diagnostics," AIP Conf. Proc., vol. 760, pp. 377-384, 2005.
129. X. Liu, Z. Dao, J. Zhu, W. Qu, X. Gong, K. Van Den Abeele, and L. Ma, "Localization of material defects using nonlinear resonant ultrasound spectroscopy under asymmetric boundary conditions," Phys. Procedia, vol. 3, no. 1, pp. 55-61, 2010.
130. L. Straka, Y. Yagodzinskyy, M. Landa, and H. Hänninen, "Detection of structural damage of aluminum alloy 6082 using elastic wave modulation spectroscopy," NDT E Int., vol. 41, no. 7, pp. 554-563, 2008.
131. P. Liu, H. Sohn, T. Kundu, and S. Yang, "Noncontact detection of fatigue cracks by laser nonlinear wave modulation spectroscopy (LNWMS)," NDT E Int., vol. 66, pp. 106-116, 2014.
132. N. Houhat and V. Tournat, "One-dimensional Parametric Study of Damage Detection in a Solid Material using a Nonlinear Wave Modulation Spectroscopy (NWMS) Technique," no. Icee, pp. 1-4, 2015.
133. S. Biwa, S. Nakajima, and N. Ohno, "On the acoustic nonlinearity of solid-solid contact with pressure-dependent interface stiffness," J. Appl. Mech. Trans. ASME, vol. 71, no. 4, pp. 508-515, 2004.
134. K. Kawashima, M. Murase, R. Yamada, M. Matsushima, M. Uematsu, and F. Fujita, "Nonlinear ultrasonic imaging of imperfectly bonded interfaces," Ultrasonics, vol. 44, no. SUPPL., pp. 1329-1333, 2006.
135. D. Donskoy, A. Sutin, and A. Ekimov, "Nonlinear Acoustic interaction on contact surfaces and its use for nondestructive testing," NDT E Int., vol. 34, pp. 231-238, 2001.
136. J.-Y. Kim, L. J. Jacobs, J. Qu, and J. W. Littles, "Experimental characterization of fatigue damage in a nickel-base superalloy using nonlinear ultrasonic waves," J. Acoust. Soc. Am., vol. 120, no. 3, pp. 1266-1273, 2006.
137. F. Amerini and M. Meo, "Structural health monitoring of bolted joints using linear and nonlinear acoustic/ultrasound methods," Struct. Heal. Monit., vol. 10, no. 6, pp. 659-672, 2011.
138. U. Polimeno and M. Meo, "Detecting barely visible impact damage detection on aircraft composites structures," Compos. Struct., vol. 91, no. 4, pp. 398-402, 2009.
139. J. J. Scholey, P. D. Wilcox, M. R. Wisnom, and M. I. Friswell, "Quantitative experimental measurements of matrix cracking and delamination using acoustic emission," Compos. Part A Appl. Sci. Manuf., vol. 41, no. 5, pp. 612-623, 2010.
140. N. Houhat and V. Tournat, "One-dimensional Parametric Study of Damage Detection in a Solid Material using a Nonlinear Wave Modulation Spectroscopy (NWMS) Technique," no. Icee, pp. 1-4, 2015.

What is claimed is:

1. A method for a structural health monitoring system, the method comprising:
connecting a first signal generator to a first actuator;
connecting a second signal generator to a second actuator;
connecting the first actuator and the second actuator to a subject structure;
generating, by the first signal generator a first signal with a first frequency, and exciting the first actuator with the first signal;
generating, by the second signal generator, a second signal with a second frequency, and exciting the second actuator with the second signal;
retrieving an output signal from the subject structure; and
analyzing the output signal of a sensor to determine whether a structural defect exists by determining whether a third frequency has been created,
the third frequency being equal to the absolute value of the result of the subtraction of the second frequency from the first frequency,
a verbal message being embedded into the first signal, which is set to the first frequency, and the second signal being set to the first frequency.

2. A method for a structural health monitoring system, the method comprising:
connecting a first signal generator to a first actuator;
connecting a second signal generator to a second actuator;
connecting the first actuator and the second actuator to a subject structure;
generating, by the first signal generator a first signal with a first frequency, and exciting the first actuator with the first signal;
generating, by the second signal generator a second signal with a second frequency and exciting the second actuator with the second signal;
retrieving an output signal from the subject structure; and
analyzing the output signal of a sensor to determine whether a structural defect exists by determining whether a third frequency has been created,
the second signal comprising a sweep frequency within a second frequency range, the lowest frequency of the second frequency range being higher than 20 kHz,
the first signal comprising a sweep frequency within a first frequency range the lowest frequency of the first frequency range being higher than 20 kHz, and
the third frequency being equal to the absolute value the result of the subtraction of the second frequency from the first frequency at a given time while the first and second frequencies vary during the sweep.

3. A method for a structural health monitoring system, the method comprising:
connecting a first signal generator to a first actuator;
connecting a second signal generator to a second actuator;
connecting the first actuator and the second actuator to a subject structure;

generating, by the first signal generator a first signal with a first frequency, and exciting the first actuator with the first signal;

generating, by the second signal generator, a second signal with a second frequency, and exciting the second actuator with the second signal;

retrieving an output signal from the subject structure; and analyzing the output signal of a sensor to determine whether a structural defect exists by determining whether a third frequency has been created, the third frequency being equal to the absolute value of the result of the subtraction of the second frequency from the first frequency, the third frequency being within a range of from 20 Hz to 20 kHz, an amplitude of the created vibrations being satisfactory to create an audible sound, and the structural defect thereby being understood without any sensor.

4. A method for a structural health monitoring system, the method comprising:

connecting a first signal generator to a first actuator;

connecting a second signal generator to a second actuator;

connecting the first actuator and the second actuator to a subject structure;

generating, by the first signal generator a first signal with a first frequency, and exciting the first actuator with the first signal;

generating, by the second signal generator, a second signal with a second frequency, and exciting the second actuator with the second signal;

retrieving an output signal from the subject structure; and analyzing the output signal of a sensor to determine whether a structural defect exists by determining whether a third frequency has been created, the third frequency being equal to the absolute value of the result of the subtraction of the second frequency from the first frequency, the first signal comprising a single frequency that is higher than 20 kHz, the second signal comprising a single frequency that is higher than 20 kHz and being different than the frequency of the first signal, the first signal and the second signal being discontinuous signals, and emission of the second signal being delayed until after emission of the first signal by a predetermined amount of time, the third frequency being within a range of from 20 Hz to 20 kHz, and an amplitude of the created vibrations being satisfactory to create an audible sound, the structural defect thereby being understood without any sensor.

* * * * *